(12) United States Patent
Alsager et al.

(10) Patent No.: US 10,023,869 B2
(45) Date of Patent: Jul. 17, 2018

(54) BIO-SENSOR FOR THE DETECTION OF SMALL MOLECULES

(71) Applicant: VICTORIA LINK LIMITED, Wellington (NZ)

(72) Inventors: Omar Ahmed Alsager, Wellington (NZ); Justin Mark Hodgkiss, Wellington (NZ); Shalen Kumar, Lower Hutt (NZ); Kenneth Patrick McNatty, Wellington (NZ)

(73) Assignee: AURAMER BIO LIMITED, Lower Hutt (NZ)

( * ) Notice: Subject to any disclaimer, the term of this patent is extended or adjusted under 35 U.S.C. 154(b) by 0 days.

(21) Appl. No.: 14/765,728

(22) PCT Filed: Feb. 5, 2014

(86) PCT No.: PCT/NZ2014/000012
§ 371 (c)(1),
(2) Date: Aug. 4, 2015

(87) PCT Pub. No.: WO2014/123430
PCT Pub. Date: Aug. 14, 2014

(65) Prior Publication Data
US 2016/0257959 A1 Sep. 8, 2016

(30) Foreign Application Priority Data

Feb. 5, 2013 (NZ) ........................................ 606696
Jun. 27, 2013 (NZ) ........................................ 612582
Dec. 3, 2013 (NZ) ........................................ 618540

(51) Int. Cl.
*C12N 15/115* (2010.01)
*C12Q 1/6811* (2018.01)
*G01N 33/53* (2006.01)
*G01N 33/543* (2006.01)

(52) U.S. Cl.
CPC .......... *C12N 15/115* (2013.01); *C12Q 1/6811* (2013.01); *G01N 33/5308* (2013.01); *G01N 33/54346* (2013.01); *C12N 2310/16* (2013.01); *C12N 2310/351* (2013.01); *C12N 2320/10* (2013.01)

(58) Field of Classification Search
CPC .............. C12N 15/115; C12N 2310/16; C12N 2310/10; G01N 33/5308
See application file for complete search history.

(56) References Cited

U.S. PATENT DOCUMENTS

2006/0014172 A1 1/2006 Muller et al.
2006/0263897 A1 11/2006 Stapert et al.
2012/0046191 A1 2/2012 Vu et al.
2012/0088232 A1 4/2012 Wanekaya et al.
2012/0302940 A1 11/2012 Ray

OTHER PUBLICATIONS

Allmyr et al., Determination of triclosan as its pentafluorobenzoyl ester in human plasma and milk using electron capture negative ionization mass spectrometry. *Anal. Chem.* 78: 6542-6 (2006).
Cho et al., Applications of aptamers as sensors. *Ann. Rev. Anal. Chem.* 2(1): 241-64 (2009).
Ellington et al., In vitro selection of RNA molecules that bind specific ligands. *Nature*, 346(6287): 818-22 (1990).
Hileman, Bisphenol A Vexations, *Chemical and Engineering News*, 85:31-3 (2007).
Javier et al., Aptamer-targeted gold nanoparticles as molecular-specific contrast agents for reflectance imaging. *Bioconjug. Chem.* 19(6): 1309-12 (2008).
Kim et al., Electrochemical detection of 17beta-estradiol using DNA aptamer immobilized gold electrode chip. *Biosens. Bioelectron.* 22: 2525-31 (2007).
Kozak et al., Advances in Resistive Pulse Sensors: Devices bridging the void between molecular and microscopic detection. *Nano Today*, 6(5): 531-45 (2011).
Olowu et al., Electrochemical aptasensor for endocrine disrupting 17β-estradiol based on a poly(3,4-ethylenedioxylthiopene)-gold nanocomposite platform. *Sensors*, 10: 9872-90 (2010).
Olowu et al., Spectroelectrochemical dynamics of dendritic poly (propylene imine)-polythiophene star copolymer aptameric 17β-estradiol biosensor. *Int. J. Electrochem. Sci.* 6: 1686-708 (2011).
Platt et al., Resistive pulse sensing of analyte-induced multicomponent rod aggregation using tunable pores. *Small*, 8: 2436-44 (2012).
Skakkebaek et al., Testicular dysgenesis syndrome: an increasingly common developmental disorder with environmental aspects. *Hum. Reprod.* 16: 972-978, 2001.
Song et al., Aptamer-based biosensors. *Trends Anal. Chem.* 27(2): 108-17 (2008).
Tuerk et al., Systematic evolution of ligands by exponential enrichment: RNA ligands to bacteriophage T4 DNA polymerase. *Science*, 249(4968): 505-10 (1990).
van Pelt et al., Ontogeny of estrogen receptor-beta expression in rat testis. *Endocrinology*, 140: 478-83 (2001).
Vandenberg et al., Hormones and endocrine-disrupting chemicals: low-dose effects and nonmonotonic dose responses. *Endocr. Rev.* 33(3): 378-455 (2012).
Willmott et al., Resistive pulse asymmetry for nanospheres passing through tunable submicron pores. *J. App. Physics*, 109(9): 094307 (2011).

*Primary Examiner* — J. E. Angell
(74) *Attorney, Agent, or Firm* — Marshall, Gerstein & Borun LLP

(57) ABSTRACT

This present invention provides methods for the detection of small molecules in samples comprising the steps a) coupling a nanoparticle (NP) or microparticle (MP) to an aptamer specific for the small molecule to be detected to form a NP-aptamer conjugate b) contacting the NP-aptamer conjugate with the sample; and c) detecting a change in the size, surface potential, or mobility of the NP-aptamer conjugate, wherein the change is indicative of the presence of the small molecule. The present invention also provides for and a biosensor comprising nanoparticles coupled to aptamers to provide nanoparticle aptamer-conjugates (NP-aptamer).

26 Claims, 16 Drawing Sheets

BIO-SENSOR FOR THE DETECTION OF SMALL MOLECULES

CROSS REFERENCE TO RELATED APPLICATIONS

This application is a U.S. National Phase Application pursuant to 35 U.S.C. § 371 of International Patent Application No. PCT/NZ2014/000012, filed Feb. 5, 2014, which claims priority to New Zealand Patent Application Nos. NZ-606696, filed Feb. 5, 2013, NZ-612582, filed Jun. 27, 2013, and NZ-618540, filed Dec. 3, 2013, the disclosures of which are incorporated herein by reference in their entirety.

TECHNICAL FIELD

This invention relates to novel bio-sensors developed comprising of nanoparticle-aptamer-conjugates (NP-aptamer) for the detection of small molecules, and their use in the detection of small molecules, and methods of detecting small molecules in a sample.

BACKGROUND

As part of normal environment testing there is an ongoing need for methods of rapidly detecting and quantifying the presence of target molecules. For example, small molecules such as endocrine disrupting compounds and hormones are often found as contaminants in the environment. Such contaminants can be found in waterways, soils, biological samples, including both plant and animals, as environmental pollutants from residential, agricultural, commercial and/or industrial applications. It is known, in some cases, that these small molecular weight compounds, such as those indicated below, together with their metabolites and/or synthetically modified variants pose a threat to the health of human and wildlife populations by mimicking the activity of endogenous hormones such as oestrogen. These molecules may act by blocking, mimicking, stimulating or inhibiting the production and function of natural hormones. The organic residues that mimic these endogenous steroidal hormones, and metabolites are lipid soluble, thus have the ability to bio-accumulate in living systems of mammals and marine species. Evidence of this has been identified in human blood plasma, breast milk, foetal tissues and biological fluids [Allmyr et al., Anal. Chem., 78: 6542-6546, 2006; Hileman, Chemical and Engineering News, 85: 31-33, 2007; Van-Pelt et al. Endocrinology, 140: 478-483, 2001; Skakkebaek et al., Human Reproduction 16: 972-978, 2001; Vandenberg et al., Endocrine Reviews, 33(3): 2012] Therefore, there is a need for new methods for easy detection of these small molecules.

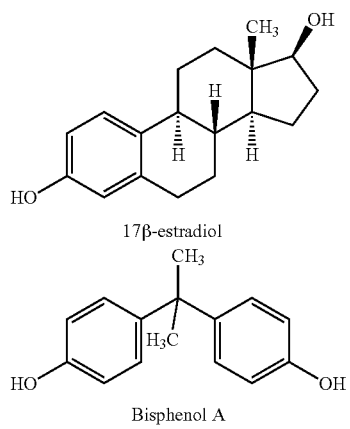

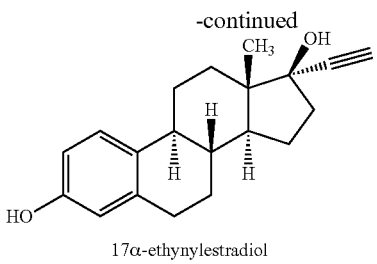

17α-ethynylestradiol

More conventional methodologies and techniques that are often used for the detection of small compounds include High Performance Liquid Chromatography (HPLC) or Gas Chromatography coupled with Mass Spectrometry (GCMS). These techniques are very useful for this purpose but the analyses can be complicated to perform and can take a long period of time to complete. Therefore, these techniques cannot be performed on site, they require specialised equipment and trained operators, and do not provide for a rapid assessment.

There is therefore a need for a convenient, quick and simple method for the detection and quantification of small molecules, especially in the area of environmental and contaminant testing.

Aptamers are single-stranded nucleic acids (ssRNA, ssDNA), which unlike traditional nucleic acids, possess unique binding characteristics to specific targets with high affinity and specificity analogous to antibodies [Tuerk, C. Gold, L., Science, 1990, 249(4968), 505-510; Ellington, A. D., Szostak, J. W., Nature, 1990, 346(6287), 818-822.] Aptamers are isolated in vitro from combinatorial oligonucleotide libraries, typically containing $10^{12}$ to $10^{15}$ oligonucleotides, and are chemically synthesised by a process known as SELEX. The oligonucleotides are subjected to a selection process for their ability to bind a specified target and over a number of selection rounds (typically 8-16 rounds); the most specific nucleic acid sequences are isolated. Depending on the techniques used in SELEX, the process might take from days to months [Cho, E. J., Lee, J. W., Ellington, A. D., Ann. Rev. Anal. Chem., 2009, 2(1), 241-264; Ellington, A. D., Ann. Rev. Anal. Chem., 2009, 2(1), 241-264.] Aptamers have been generated for a wide range of targets, ranging from ions to entire cells. The use of an in vitro process enables the generation and selection of aptamers that can bind toxic targets, which are not possible by immunologically initiated recognition elements, such as antibodies. The small size of aptamers (generally <3 nm in a coiled conformation) also makes them more readily applicable to surface-based aqueous sensing purposes in comparison to antibodies (approximately >10 nm in size) [Song, S., et al., Trends in Analytical Chemistry, 2008, 27(2), 108-117].

Baker et al., [Olowu, R. A.; Arotiba, O.; Maliu, S. N.; Waryo, T. T.; Baker, P.; Iwouoha, E., Sensors, 2010, 10, 9872] have previously shown that electrochemical DNA aptasensors developed from poly(3,4-ethylenedioxythiophene) (PEDOT) doped with gold nanoparticles (AuNP) have high affinity for the detection of 17β-estradiol. The PEDOT-AuNP are synthesised for the immobilisation of 17β-estradiol. This PEDOT-AuNP is able to reliably detect 17β-estradiol in the range of 0.1 nM-100 nM, with a detection limit of 0.02 nM.

In addition, Baker et al. [Olowu, R. A., Ndangili, P. M., Baleg, A. A, Ikpo, C. O., Njomo, N., Baker, P, Iwuoha, E., Int. J. Electrochem. Sci., 2011, 6, 1686] have also prepared and shown an aptamer biosensor developed from a dendritic first generation poly(propyleneimine)-polythiophene copolymer (shown below)-functionalised gold electrode via biotin-avidin interaction in the determination of endocrine disrupting compounds, especially 17β-estradiol.

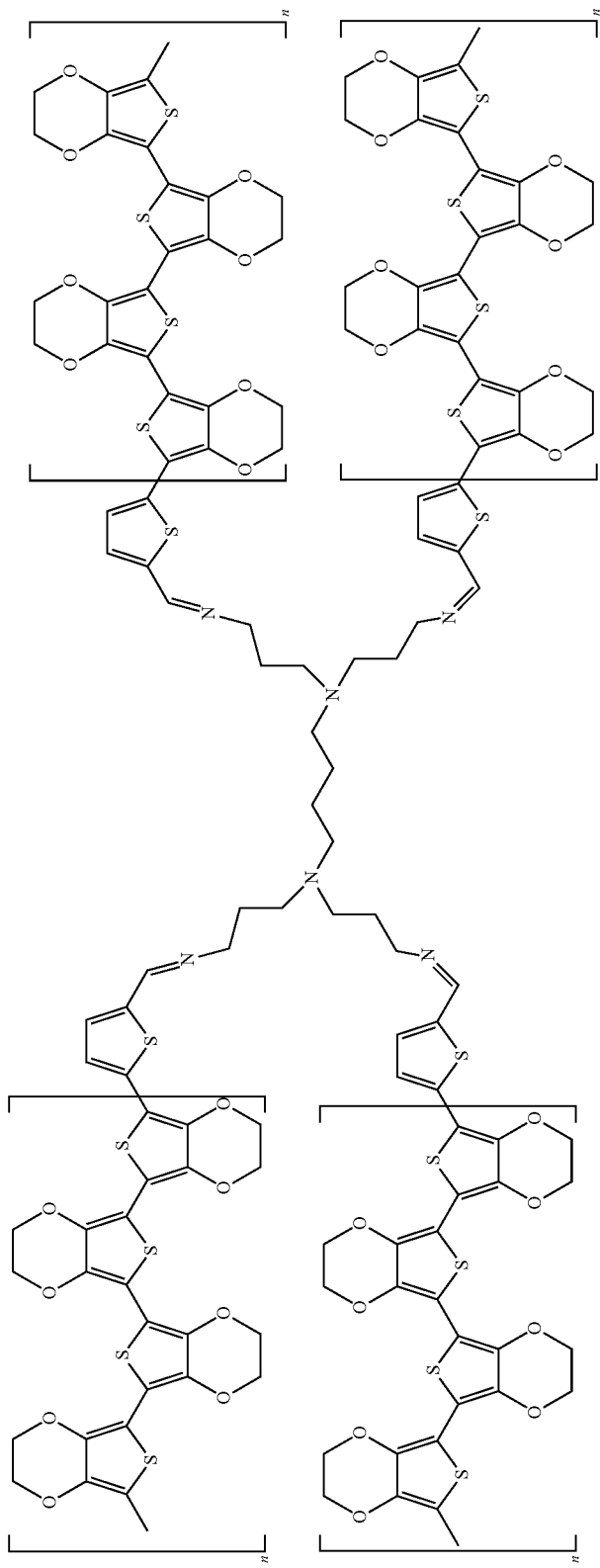

The sensor platform and aptasensor were investigated using techniques such as scanning electron microscopy, Fourier transform infrared spectroscopy, electrochemical impedance spectroscopy, cyclic voltammetry and square wave voltammetry. The authors report that the response in the detection of 17β-estradiol was measured using square wave voltammetry with a linear range of the sensor of 0.1 to 100 nM. In addition, this particular aptamer is specific only to 17β-estradiol.

Lee and Gu et al. [Kim, Y. S., Jung, H. S., Matsuura, T., Lee, H. Y., Kawai, T., Gu, M. B. *Biosensors and Bioelectronics*, 2007, 22, 2525] report the synthesis and use of ssDNA aptamer based electrochemical biosensors by immobilisation of the ssDNA aptamer on a gold electrode chip in the detection of 17β-estradiol. The detection levels of 17β-estradiol are reported to be in the range of from 1000 to 0.1 nM. However, the authors report at lower concentrations, in the range of 0.01 nM to 0.001 nM, their measurements may not be related to the binding of the aptamer to the substrate which makes this particular method unreliable.

US 2012/0088232 teaches a method for the detection of target molecules in patient samples at a point of care location using a point of care lateral flow device. The point-of-care lateral flow device specifically detects cancer markers and proteins, in particular p-glucoprotein (Pgp), by utilising aptamers that have been labelled with appropriate tags such as fluorophores. The aptamers are conjugated to solid supports, such as nanoparticles, and the presence of the target substrate molecules are quantified using techniques, including dynamic light scattering. In this case, dynamic light scattering measures increases in particle sizes associated with aptamer-substrate complex formation.

Any reference to prior art publications within this specification does not constitute an admission that such references form part of the common general knowledge in the art in any country.

It is an object of the present invention to provide a method for the rapid detection of small molecules in a sample, or to at least provide the public with a useful alternative.

The inventors of the present invention have surprisingly found that NP-aptamer-conjugates disclosed herein can be successfully applied to the detection of small molecules at low levels providing for quick confirmation of the presence of these small molecules in isolated samples.

STATEMENTS OF INVENTION

In a first aspect, the present invention provides a method for the detection of small molecule in a sample comprising the steps:
a) coupling a nanoparticle (NP) or microparticle (MP) to an aptamer specific for the small molecule to be detected to form a NP-aptamer conjugate;
b) contacting the NP-aptamer conjugate with the sample;
c) detecting a change in the size, surface potential, and/or mobility of the NP-aptamer conjugate, wherein the change is indicative of the presence of the small molecule.

In an embodiment of the first aspect, step (a) of the method may optionally comprise detecting a change in the size, surface potential, and/or mobility to ensure the aptamer has coupled to the NP or MP.

In another embodiment of the first aspect, the change in step (c) is a reduction in the size of the in the size, surface potential and/or mobility of the NP-aptamer conjugate when the NP-aptamer conjugate contacted in the presence of the small molecule.

In another embodiment of the first aspect, the change in the size, surface potential, and/or mobility of the NP-aptamer is detected using dynamic light scattering (DLS) or Resistive Pulse Sensing (RPS). Other techniques capable of measuring changes in particle size, surface potential and/or mobility can also be used, including nanoparticle tracking analysis.

Preferably, in step (b) of the first aspect, contacting the NP-aptamer conjugate with the sample includes one or more surfactants. The surfactant may be a detergent. In particular, the detergent may be an anionic detergent, a cationic detergent or a non-ionic detergent. Preferably, the detergent can be a non-ionic detergent selected from IGEPAL™ ((Octylphenoxy)polyethoxyethanol), Tween 20 (Polyethylene glycol sorbitan monolaurate), Tween 40 (Polyethylene glycol sorbitan monopalmitate), Tween 80 (Polyethylene glycol sorbitan monooleate), Triton X-100 (4-(1,1,3,3-Tetramethylbutyl)phenyl-polyethylene glycol), Nonidet p40 ((Octylphenoxy)polyethoxyethanol) and substitutes of Nonidet p40. It is preferred that the detergent is IGEPAL™ ((Octylphenoxy)polyethoxyethanol).

The NP-aptamer conjugate may comprise a ratio in the number of NP:aptamer of from about 1:1,000,000 up to about 1:1. More preferably, a NP:aptamer ratio of from about 1:50 to about 1:10000, even more preferably, a NP:aptamer ratio of from about 1:500 to about 1:2000.

The nanoparticle is of size about 5 nm to about 5 microns, preferably about 50 nm to about 500 nm, even more preferably about 100 nm to about 250 nm.

Preferably, the nanoparticle is selected from a gold, palladium, polystyrene, and latex nanoparticle. More preferably, the nanoparticle is a polystyrene nanoparticle.

The nanoparticle may also be an amide/carboxylic acid functionalised nanoparticle. Preferably, the nanoparticle is a carboxylic acid functionalised nanoparticle.

The nanoparticle is preferably a carboxylic acid functionalised polystyrene nanoparticle.

The nanoparticle may include a magnetic element. For example, it may include a magnetic iron core.

In an embodiment of the first aspect, the small target molecule to be detected may be a pollutant. Preferably, the small molecules are selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. More preferably, the small molecule to be detected is selected from 17β-oestradiol, testosterone, progesterone, and adenosine.

The small molecule to be detected may also be hormone or a marker of a condition of disease in a body. For example, the method could be used in the detection of hormones and/or metabolites to establish fertility, or status in an animal. Alternatively, the method can be used to detect known markers of disease, for example overexpression of a cancer gene to detect cancer, detection of molecules associated with infection, or to establish levels of specific metabolites associated with a particular condition.

The sample containing the small molecule to be detected may be an environmental sample, for example a water sample, soil sample, or even a plant sample. The method can also be used to detect a small molecule in a sample from an animal, for example a tissue sample, a hair or wool sample, a urine sample, a blood sample, saliva sample or a faecal sample. In one aspect, the method could be used to detect the presence of a contaminant in livestock, but could also be used to detect changes within an animal, for example changes in hormone levels in the blood of tissue to establish when an animal is in heat, or the detection of marker compounds associated with a disease or condition.

In a second aspect, the invention provides for a biosensor comprising:

(a) a nano- or micro-particle and;
(b) an aptamer,
wherein the nanoparticle or microparticle is coupled to the aptamer to provide an NP-aptamer conjugate, and
wherein there is a change in the size, surface potential, and/or mobility of the NP-aptamer conjugate when the NP-aptamer conjugate is contacted with a small molecule in a sample.

In an embodiment of the second aspect, the change in size in step (b) may be a reduction in the size, surface potential, and/or mobility of the NP-aptamer conjugate when the NP-aptamer conjugate is contacted with the small molecule.

The biosensor may be used in conjunction with techniques selected from RPS, DLS and combinations thereof, to detect the change in the size, surface potential, and/or mobility of the NP-aptamer conjugate. Other techniques capable of measuring changes in particle size, surface potential and/or mobility tracking may be used, including nanoparticle tracking analysis.

Preferably a detergent or surfactant, or combinations thereof, are optionally used to assist in the detection of changes in the size, surface potential, and/or mobility of the NP-aptamer conjugate, when contacted with a small molecule. The surfactant may be a detergent. In particular, the detergent may be an anionic detergent, a cationic detergent or a non-ionic detergent. Preferably, the detergent can be a non-ionic detergent selected from IGEPAL™ ((Octylphenoxy)polyethoxyethanol), Tween 20 (Polyethylene glycol sorbitan monolaurate), Tween 40 (Polyethylene glycol sorbitan monopalmitate), Tween 80 (Polyethylene glycol sorbitan monooleate), Triton X-100 (4-(1,1,3,3-Tetramethylbutyl)phenyl-polyethylene glycol), Nonidet p40 ((Octylphenoxy)polyethoxyethanol), and substitutes of Nonidet p40. It is preferred that the detergent is IGEPAL™ ((Octylphenoxy)polyethoxyethanol).

The NP-aptamer conjugate may comprise a ratio in the number of NP:aptamer of from about 1:1,000,000 up to about 1:1. More preferably, a NP:aptamer ratio of from about 1:50 to about 1:10000, even more preferably, a NP:aptamer ratio of from about 1:500 to about 1:2000.

The nanoparticle is of a size of about 5 nm to about 5 microns, preferably about 50 nm to about 500 nm, and even more preferably about 100 nm to about 250 nm.

In an embodiment of the second aspect, the nanoparticle may be selected from a gold, palladium, polystyrene, and latex nanoparticle.

Preferably, the nanoparticle is a polystyrene nanoparticle. Alternatively, the nanoparticle may also be an amide/carboxylic acid functionalised nanoparticle.

Alternatively preferably, the nanoparticle is a carboxylic acid functionalised nanoparticle.

The nanoparticle is preferably a carboxylic acid functionalised polystyrene nanoparticle.

The nanoparticle may include a magnetic element. For example, it may include a magnetic iron core.

In yet a further embodiment of the second aspect, the small target molecule to be detected may be a pollutant. Preferably the small molecules are selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. More preferably, the small molecule to be detected is selected from, 17β-oestradiol, testosterone, progesterone, and adenosine.

The small molecule to be detected may also be hormone or a marker of a condition of disease in a body. For example, the method could be used in the detection of hormones and/or metabolites to establish fertility, or status in an animal. Alternatively, the method can be used to detect known markers of disease, for example overexpression of a cancer gene to detect cancer, detection of molecules associated with infection, or to establish levels of specific metabolites associated with a particular condition.

In another embodiment of the second aspect, the sample may be an environmental sample, for example a water sample, soil sample, or even a plant sample. The method can also be used to detect a small molecule in a sample from an animal, for example a biological sample, a tissue sample, a hair or wool sample, a urine sample, a blood sample, saliva sample or a faecal sample. In one aspect the method could be used to detect the presence of a contaminant in livestock, but could also be used to detect changes within an animal, for example changes in hormone levels in the blood of tissue to establish when an animal is in heat, or the detection of marker compounds associated with a disease or condition.

In a third aspect, the invention provides the use of a biosensor described herein in the detection of a small molecule in a sample.

In an embodiment of the third aspect, the invention provides the use, of the in combination with a technique selected from RPS, DLS and combinations thereof. Alternatively, other techniques may be used to measure changes in change in the size, surface potential, and/or mobility including nanoparticle analysis.

In an embodiment of the third aspect, the use of the biosensor optionally includes a detergent or surfactant. The surfactant may be a detergent. In particular, the detergent may be an anionic detergent, a cationic detergent or a non-ionic detergent. Preferably, the detergent can be a non-ionic detergent selected from IGEPAL™ ((Octylphenoxy)polyethoxyethanol), Tween 20 (Polyethylene glycol sorbitan monolaurate), Tween 40 (Polyethylene glycol sorbitan monopalmitate), Tween 80 (Polyethylene glycol sorbitan monooleate), Triton X-100 (4-(1,1,3,3-Tetramethylbutyl)phenyl-polyethylene glycol), Nonidet p40 ((Octylphenoxy)polyethoxyethanol), and substitutes of Nonidet p40. It is preferred that the detergent is IGEPAL® ((Octylphenoxy)polyethoxyethanol).

Preferably, the use of the biosensor is in the detection of small molecules. Preferably, the small molecule is a pollutant. Preferably, the small molecules are selected from chemicals that mimic hormones, hormones, naturally occurring phytoestrogens, narcotics and metabolites thereof. Preferably, the small molecule is an endocrine disrupting compound, a steroidal sex hormone, metabolites or synthetic variants thereof. More preferably, the small molecule is selected from endocrine disrupting compounds, and metabolites thereof. Even more preferably, the small molecules are selected from 17β-oestradiol (E2); oestrone; oestriol; androstenedione; testosterone; dihydrotestosterone; pregnenolone; progesterone; 17α-hydroxyprogesterone, 17α- ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. More preferably, the small molecule to be detected is selected from 17β-oestradiol, testosterone, progesterone, and adenosine.

In an embodiment of any one of the aspects of the invention, the invention provides for an aptamer comprising the sequence: 5'-ATACGAGCTTGTTCAATAC-GAAGGGATGCCGTTTGGGCCCAAGTTCGGCATAG TGTGGTGTAGTAAGAGCAATC-3'(SEQ ID NO: 1), or a sequence having 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity.

In an embodiment of any one of the aspects of the invention, the aptamer comprising the sequence is: $NH_2$ $(CH_2)_6$ATACGAGCTTGTTCAATACGAAGGGATGC-CGTTTGGGCCCAAGTTCGG CATAGTGTGGTGTAG-TAAGAGCAATC (SEQ ID NO: 1) or a sequence having 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity.

In yet another embodiment of any one of the aspects of the invention, the aptamer comprising the sequence may optionally include a fluorescent tag. The tag may Cy5.5, alsi known by its IUPAC name as 1H-Benz[e]indolium, 2-[5-[3-[6-[(2, 5-dioxo-1-pyrrolidinyl)oxy]-6-oxohexyl]-1,3-dihydro-1,1-dimethyl-6,8-disulfo-2H-benz[e]indol-2-ylidene]-1,3 pentadien-1-yl]-3-ethyl-1,1-dimethyl-6,8-disulfo-, inner salt, sodium salt (1:3). It should be appreciated by those of skill in the art that any fluorescent tag known in the art may be used, and is not limited to either 3' and/or 5' positions of an aptamer.

In yet another aspect, the invention provides a method for the detection of adenosine at low levels using an adenosine aptamer (27-mer oligonucleotide) (Kim, J., Kim, I. Y., Choi, M. S., Wu, Q., *Chem. Commun.*, 2009, 4747-4749), and using the techniques and methods described herein. Preferably, the adenosine is detected at levels of about 500 nM or below.

DETAILED DESCRIPTION

Unless the context clearly requires otherwise, throughout the description and the claims, the words "comprise", "comprising" and the like, are to be construed in an inclusive sense as opposed to an exclusive or exhaustive sense, that is to say, in the sense of "including, but not limited to".

The term "aptamer" as described herein is intended to mean a single strand of RNA or DNA that specifically binds to particular target molecules. The term "aptamer" relates to polynucleotide or oligonucleotide sequences. The terms "polynucleotide" or "oligonucleotide" may be used interchangeably and is a term commonly used and understood within the art. Those skilled in the art will readily understand that variation in the sequence code of the aptamer may be varied by standard methodology without substantially affecting the binding of the substrate to the NP-aptamer conjugate.

The term "conformational changes" means a change in the conformational form of the aptamer, for example, a change from a tightly folded structure to a loose linear-type structure that results in opening up of the binding site, or from a loose linear-type structure to a tightly folded structure. This type of alteration would be readily understood by those skilled in the art.

The term "sample" is intended to mean a sample isolated or collected from an environmental or biological source and is located ex vivo. The sample may be of biological origin, isolated from an animal or may be collected from the environment. Sources of samples may include for example soils, waterways, tissue, blood, urine, saliva, faeces, hair and wool.

The term "animal" is intended to mean human and non-human subjects. For example, humans; domesticated stock including cows, sheep, goats, horses, pigs; domesticated pets including cats, dogs; wild animals including monkeys, birds, amphibians, reptiles; aquatic life forms such as fish.

The term "small molecules" is intended to mean compounds of simple molecular structure with a Mw of from about 60 to about 2000 g ma', preferably in the range of from about Mw 100 to 500 g $mol^{-1}$, more preferably of from about 150 to 350 g $mol^{-1}$. The molecular weight of such compounds and the calculation of the molecular weights are well known to those of skill in the art. Such compounds include hormone mimics, hormones, naturally occurring phytoestrogens, narcotics and metabolites thereof, organohalides and compounds such as 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof.

The term "wetting" is intended to mean the penetration of a liquid into a nanopore such that the pore becomes filled with liquid and results in complete filling of the pore with liquid, and the ability to observe a constant ionic current through the pore.

The term "NP-aptamer conjugate" is also intended to include microparticle-aptamer conjugates. That is, either nanoparticles or microparticles may be used and the term is not intended to exclude microparticles.

The invention as described provides for a novel method of using aptamers to rapidly detect the presence of a target molecule in a sample and a novel biosensor for the detection of small molecules.

Without wishing to be bound by theory, the method works by coupling an aptamer capable of selectively binding the target compound (where the target compound is a small molecule) to a nanoparticle (NP) or microparticle (MP), so as to form a NP-aptamer conjugate. In doing so, there is a detectable increase in the size and/or surface potential of the NP component of the NP-aptamer conjugate, which confirms the formation of the NP-aptamer conjugate.

The NP-aptamer conjugate is then contacted with a sample. When a target molecule is present in the sample above the threshold concentration, the aptamer component of the NP-aptamer conjugate will bind in varying degrees to the target molecule. The consequence of this binding will result in a detectable reduction in the overall size of the NP-aptamer conjugate and a change in the overall surface potential (an example of this is seen in FIGS. 3-7). The measurement of these changes in the NP-aptamer conjugate size or the NP-aptamer conjugate size, surface potential, and/or mobility in the sample, allows for a very quick determination of the presence of the target molecule in the sample. The change in NP-aptamer size, surface potential, and/or mobility on binding the substrate and forming the NP-aptamer-substrate conjugate is proportional to the concentration of the target molecule. Therefore, the test can also rapidly establish the concentration of the target molecule, by comparison with standards of known concentrations.

The test has also been found to be extremely sensitive, detecting the presence of very low amounts of the target molecule, as low as 1 nM.

Nano-Particle—Aptamer Conjugates

The aptamer of the present invention is prepared by standard methodology, for example by preparing the library of short oligonucleotides using SELEX. The oligonucleotides are subjected to a selection process for their ability to bind a specified target, and over a number of selection rounds (typically 8-18), the most specific nucleic acid species are isolated. [Cho, E. J., Lee, J. W., Ellington, A. D., *Ann. Rev. Anal. Chem.*, 2009, 2(1), 241-264; Ellington, A. D., *Ann. Rev. Anal. Chem.*, 2009, 2(1), 241-264.]

bare NP sample (1). This is achieved by combining one or more aptamers to the NP to form a single larger NP-aptamer conjugate. This then results in the aptamer being attached to a particle which can be accurately measured using techniques known in the art. For example, the change in size can be detected by dynamic light scattering (DLS), Resistive Pulse Sensing (RPS), particle tracking analysis, or any other suitable detection method according to standard literature procedures [Platt, M., Willmott, G. R., Lee, G. U., *Small*, 2012, 8, 2436; Song, S., et al., *Trends in Analytical Chemistry*, 2008, 27(2), 1087; Willmott, G. R, Parry, B. E. T., *J. App. Physics*, 2011, 109(9); Kozak, D., et al., *Nano Today*, 2011, 6(5), 531; Javier, D. J., et al., *Bioconjugate Chemistry*,

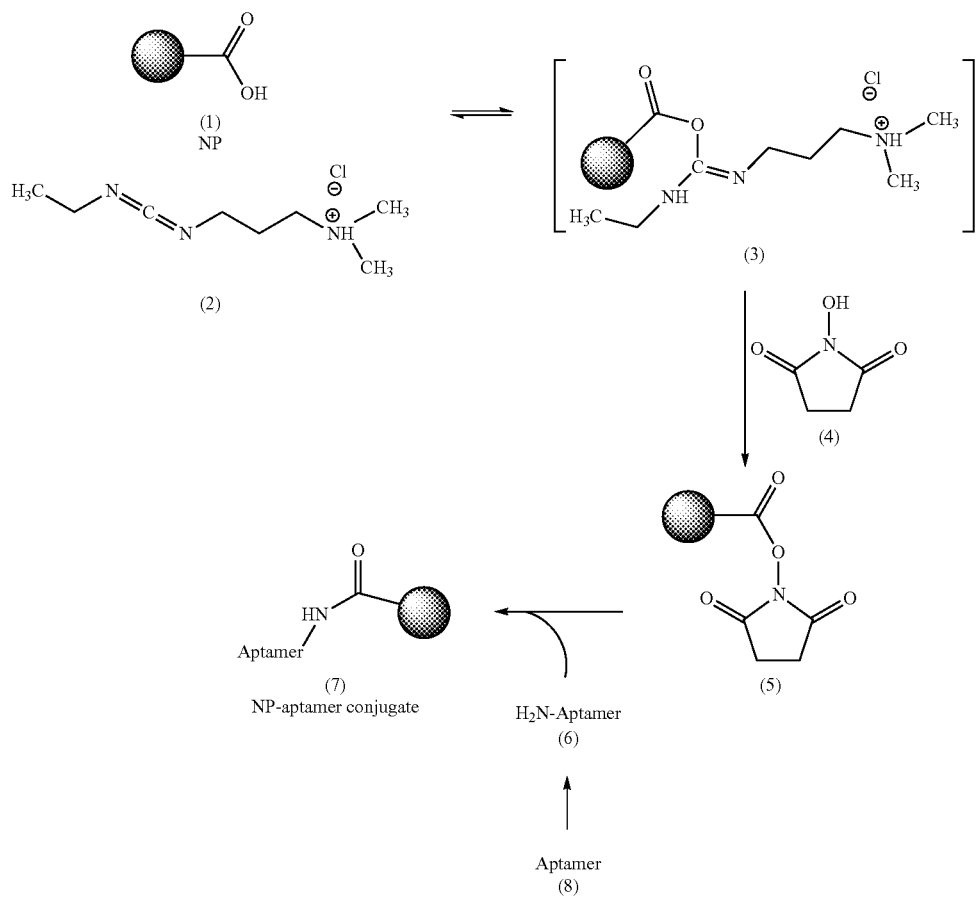

Scheme 1

The NP-aptamer conjugate of formula (7) is prepared by coupling the nanoparticle carboxylic acid of formula (1) with 1-ethyl-3-(3-dimethylaminopropyl) carbodiimide of formula (2) to form O-acyl isourea intermediate of formula (3). The compound of formula (3) is then reacted with NHS to form intermediate of formula (5). Aptamer (8) (as shown in FIG. 2) is modified with a primary amino group so as to form the $H_2N$-aptamer (6) with a terminal amino moiety. Reacting this $H_2N$-aptamer (6) with compound (5) forms the aptamer-nanoparticle conjugate of general formula (7) as shown in scheme 1. If required, compounds (1), (5) and (7) can be isolated from the reaction mixture by centrifuging at speed of 14,000 rpm for at least 20 minutes.

The $H_2N$-aptamer of formula (6) is judged to have been successfully tethered to the nanoparticle (1) by an increase in the final physical size and/or change in surface potential of the NP-aptamer conjugate (7) when compared with the 2008, 19(6), 1309]. Further to this, DLS and/or RPS and/or particle tracking analysis can be used to evaluate the changes in surface potential of the NPs as the $H_2N$-aptamer (6) is coupled to form (7). RPS results show that there is 15 nm increase in the diameter of the NP-aptamer conjugate (7) disclosed herein when the NP and $H_2N$-aptamer (6) are coupled together.

The advantage of RPS over current conventional methodologies is that it allows for analysis of a sample on a particle-per-particle basis. Analysis times for RPS are significantly quicker with analysis times in the range of from 2 to 6 minutes, compared to conventional techniques that have analysis time from minutes to many hours or days.

In addition, RPS phase analysis light scattering allows for the measurement of changes in the surface potential by placing (7) in a capillary cell and applying external voltage across gold electrodes. By illuminating this with laser light, the light is scattered and the surface potential can be measured because the frequency of the scattered light is proportioned to the electrophoretic mobility. In addition, when the negatively charged aptamer of formula (6) forms (7), the ζ-potential (a measurement of surface potential) of (7) becomes more negative compared with (1) as shown in FIG. 14. In the case of RPS, population (7) is compared with (1) by lower particle mobilities and longer pulse durations as shown in FIG. 11.

Any nanoparticle or microparticle is suitable for use in the invention, provided it can be tethered to one or more aptamers, and is inert to any binding of the aptamer to the target molecule. Suitable nanoparticles or microparticles include, but are not limited to gold, palladium, polystyrene, or latex. The nanoparticle or microparticle may also be an amide/carboxylic acid functionalised nanoparticle or microparticle such as carboxylic acid functionalized polystyrene particles.

Detection of Target Molecules

The method of the present invention, particularly that exemplified, is useful in the detection of small molecules in a sample by using a NP-aptamer conjugate and measuring conformational and surface potential changes when the NP-aptamer conjugate binds the target substrate molecule to form the NP-aptamer-substrate conjugate (FIG. 5).

Coupling the aptamer to the NP increases the overall size and diameter of NP-aptamer conjugate as well as changing its surface potential. However, when the NP-aptamer conjugate binds to the substrate to form the NP-aptamer-substrate conjugate, it undergoes a contraction in the overall size and diameter and exposes a different density of surface potential. Without wishing to be bound by theory, when the NP-aptamer conjugate disclosed herein binds small target molecules, the aptamer component of the NP-aptamer conjugate undergoes a conformational change. For example, the overall size, shape, and/or the surface potential of the aptamer contracts and become smaller by folding around its specific target. These conformational changes are triggered by interactions of the target molecule with the aptamer tether of the NP-aptamer conjugate, as is shown in FIG. 5. Detection of this change provides a method of detecting when the target substrate molecule binds to the NP-aptamer.

In order to establish that the contraction in diameter of the NP-aptamer conjugate on binding the substrate is due to the binding of the substrate, the bare NP (for example compound (1) without any aptamer) was assessed in the presence and in the absence of 50 nM E2 substrate as is shown in FIG. 6. The results show that no change in size occurs; concluding that any change is due to the presence of the aptamer tethered to the NP.

This is further exemplified in a second control experiment. The NP-aptamer conjugate (7) was exposed to blank BWB. There was no contraction in size or change in the surface potential, confirming that for the change in size to occur NP-aptamer conjugate (7) requires the substrate to be present. Therefore, these changes in size and/or surface potential are a direct result of the NP-aptamer conjugate binding to the substrate (FIG. 15) and forming the NP-aptamer-substrate conjugate.

It will be appreciated that the present invention is suitable for use in detecting any target compound. All that is required is to produce an aptamer (using known methods as described above) that specifically binds to the target molecule. Ideally the target molecule is a small molecule, that is, it is sufficiently smaller than the NP-aptamer conjugate to result in a reduction in the conjugate size when the aptamers bind the target compound.

It is also preferred that the sample be in solution to allow the NP-aptamer conjugate to bind and the change in size detected. It will be appreciated that the method is particularly suitable for the detection of contaminates or pollutants in environmental samples, but not limited to, for example water samples, soil, biological samples, including plant or animal tissue, faecal, salivary, urine samples, or any suitable environmental sample suspected of containing the target molecule that is either in an aqueous phase or can be converted or extracted into an aqueous phase.

However, it will be appreciated that the method can used to detect any compound in a sample. Accordingly the invention is not limited to a single application but covers the detection of any target compound in solution. This can include for example, the detection of hormones or metabolites in a biological sample to establish the status of an animal. This could be the detection of hormones to establish the fertility of an animal, including a human.

Alternatively, many markers are known to be associated with disease. The current method could be used in the detection of these markers for diagnostic purposes. For example, many gene markers are known to be associated with cancer, and therefore the method could be used to detect gene expression in a sample from a patient to diagnose cancer. Similarly, other markers, including metabolites are known to be associated with various diseases or conditions, and the method is suitable for use in the detection or monitoring of any such markers for the purpose of diagnosis, prognosis or monitoring of that disease or condition.

The inventors have surprisingly and advantageously found that the NP-aptamer conjugate of general formula (7) recognises small molecules, in particular endocrine disrupting compounds and members of the oestrogenic compound family.

In particular, the small molecules to be detected can be endocrine disrupting compounds such as 17β-oestradiol (E2), oestrone, oestriol, androstenedione, testosterone, dihydrotestosterone, pregnenolone, progesterone, 17α-ethynylestradiol, 17α-hydroxyprogesterone, synthetic steroids such as diethylstilboestrol (DES), ethinyloestradiol and norethindrone; naturally occurring phytoestrogens such as isoflavones, lignans and coumestans; organohalides, organochlorines, polychlorinated organic compounds, polychlorobiphenyl (PCB), alkylphenols, alkylphenol ethoxylates, phthalates, bisphenol-A (BPA), Bis (4-hydroxyphenyl) methane, adenosine, cholesterol, triclosan; and narcotics such as cocaine and heroin.

In particular, the small molecules can be detected in environmental samples, such as domestic water samples, agricultural water samples, industrial water samples, soil samples, isolated biological samples, and samples taken from animals.

The inventors have surprisingly and advantageously been able to detect concentrations of E2 in the range of from 1-100 nM using various numbers of aptamer tethered onto the NP (i.e. the ratio of the number NP:aptamer) as shown in FIGS. 6, 7 and 8 and also adenosine at levels as low as 500 nM as shown in FIGS. 9a and 9b. Lower aptamer densities than in this example can also be used to detect lower concentrations of E2.

As the concentration of E2 increases, the aptamer coating on the NP contracts due to folding around the target substrate molecule. In addition, the pulse duration time (FWHM) measured by RPS increases when the NP-aptamer is bound to E2. In RPS, the FWHM is related to surface potential, where lower magnitude of surface potential results in slower motion and therefore longer FWHM. In the present case, the increase in pulse duration is consistent with the observation via phase analysis light scattering that binding E2 is associated with less negative surface potential of the NP-aptamer conjugate (see FIG. 16).

Use of Detergents

The inventors have also surprisingly found that detergents and surfactants at an appropriate concentration level can be used in order to achieve enhanced sensitivity towards small target molecules. Without wishing to be bound by theory, the presence of a detergent and/or a surfactant assists in the ability of the aptamer to specifically bind to the target molecule Selective NP-aptamer conjugate target binding is optimally activated under the same detergent conditions as those for which the aptamer is generated using SELEX. Without wishing to be bound by theory, the presence of the detergent affects the charge distribution of the aptamer by removal of weakly bound non-specific targets from the NP-aptamer surface, and thereby enhancing its conformational energetics.

Detergents also assist in analysis of the results using RPS by wetting the nanopore membrane and permitting an ionic current to pass through the pore.

TABLE 1

Effect of different detergents on RPS sensing.

| Name of surfactant | Type of surfactant | Reason of not working In RPS |
|---|---|---|
| None | — | No wetting occurred and therefore no running |
| SDS | Anionic | Wide distribution of size of NP-aptamer conjugate, preventing from resolving size change |
| DOD | Cationic | No blockade events observed (no proper wetting) |
| ECD | Non-ionic | No blockade events observed (no proper wetting) |
| Tween-20 | Non-ionic | No increase in size was observe |
| IGEPAL ® | Non-ionic | Proper wetting and increase in size when aptamer coupled to NPs and possible detection of E2 |

Methods of Detection

The present method involves the detection of the conformational change on the surface of the NP-Aptamer conjugates. Any suitable methods for detecting a conformation change as known in the art may be used. Methods used may include, but are not limited to, the following techniques:

Resistive Pulse Sensing (RPS)

Resistive pulse sensing experiments involve the detection and analysis of particles as they traverse through a channel or pore separating two cells of a conducting electrolyte. An external voltage is applied across the system and a base line current passes through the pore and the resistance of the pore is monitored. As a particle passes the pore construction, it disrupts the ionic current causing an event (so-called blockade). The blockade duration (FWHM) and magnitude are related to the particle surface potential and size respectively. Tuneable nanopore RPS is the latest advancement of the field of RPS utilising a stretchable polyurethane membrane containing a conical nanopore (made by a puncturing with a tungsten needle). This technique is seen for example in a device called the qNano made by Izon Nanoparticles. Tuneable nanopore RPS has numerous advantages being able to generate particle-per-particle analysis and eliminating clogging difficulties associated with fixed nanopore [7-9] (Refer to FIG. 1).

In a typical tuneable nanopore RPS experiment, ~500 NPs are analysed (generating 500 blockade events). The analysis time ranges from 2 to 6 minutes depending on the particle concentration and the system conditions. Then the size is calculated based on a comparison against well-known particle size run under the same experimental conditions (pore-opening, applied voltage, pressure and suspending medium). As shown in FIG. 4, the data is expressed as a scatter plot representing the size and FWHM (X and Y axis respectively) and histograms of size and FWHM are built.

Dynamic Light Scattering and (DLS) and Phase Analysis Light Scattering

Dynamic light scattering (DLS) (also known as photon correlation spectroscopy, PCS) is a technique measures the size of a NPs suspension based on the random changes in the intensity of their scattered light. A small particle in a colloidal system undergoes a thermal motion (called Brownian motion) which causes the fluctuation in the intensity of the scattered light.

The sample is illuminated by a light sourced from a laser, then the scattered light by the particles is collected (at a given angle, 90°) and the fluctuation of the intensity of the scattered light is monitored over time (shown in FIG. 3). The data is introduced in real time to a correlator that calculates the decay time which, is in turn, used to calculate the translation diffusion coefficient of the particles (Dt). Dt is used in Stokes-Einstein relation (shown below) to find the hydrodynamic size of the particles (NPs+ bound ions in suspension). Finally, as shown in FIG. 1, the size distribution of NPs is obtained (NPs have to be spherical and mono-disperse). Ref: Malvern Instruments Ltd (2007) Technical information provided for the Zeta-sizer Nano.

$$Dh = KB \, T/a\pi\eta \, Dt$$

Dh: hydrodynamic size, KB: Boltzmann constant, T: temperature, $\eta$ viscosity and Dt: translational diffusion coefficient.

Surface potential (specifically, the $\zeta$-potential) is obtained in light scattering method (phase analysis light scattering, PALS) in a related but slightly different manner to size measurement. The sample containing NPs is placed in a capillary cell and an external voltage is applied across the cell using gold electrodes. The particles will move towards to the oppositely charged electrode. When the sample is equilibrated with the opposite acting forces of particle's movement, the sample is illuminated with laser light and the scattered light collected at 17°. In PALS, the shift in phase due to particles movement causes the intensity fluctuation of the scattered light. The frequency of the scattered light is proportional to the electrophoretic mobility (UE) of the particles. The data is introduced to a correlator in real time and the UE is calculated. Finally, $\zeta$-potential is calculated using Henry equation (shown below). Under a given experimental condition the electrolyte viscosity ($\eta$), medium dielectric constant ($\in$) and Henry's function ($f(Ka)$=1.5 for a moderate electrolyte concentration) are known and $\zeta$-potential is generated as a histogram for a given population. Ref: Ref: Malvern Instruments Ltd (2007) Technical information provided for the Zeta-sizer Nano, chapter 16.

$$UE = 2 \in \zeta\text{-potential } f(Ka)/3\eta$$

Particle Tracking Analysis (PTA)

Particle tracking analysis (including nanoparticle tracking analysis) also exploits the analysis of Brownian motion to measure the size of the particles undergoing the motion. Like with DLS measurements, the measured speed of particle Brownian motion is related to the particle size via the Stokes-Einstein relation (above).

PTA differs from DLS in the means by which particle Brownian motion is measured. In PTA, the solution containing particles is imaged in an ultramicroscope and the particle motion is tracked over time frame-by-frame. PTA is therefore a particle-by-particle technique (like RPS) rather than an ensemble technique (like DLS).

Quantification of the Concentration Levels of Substrate

The detectable change in the size of the NP-aptamer conjugate is dependent on the concentration of the target molecule in the sample, for example the larger the change measured, the higher the levels of target molecule present. Therefore, it is possible to utilise series of sample containing known amounts of the target molecule in order to produce a standard curve or equation by which the concentration of the target molecule in the test sample can be established. Methods for establishing sample concentration are well known in the art.

The present invention provides a method by which the presence of a target molecule in a sample can be very rapidly established along with its concentration. The method requires that the NP-aptamer conjugate is mixed with the sample and then the change in aptamer size is detected. This change may be detected using RPS, DLS or any other suitable method or system.

Utilisation of techniques such as dynamic light scattering (DLS) and Resistive Pulse Sensing (RPS), involves the use of small readily available machines that can potentially be used in the field, or at a convenient location, and does not require high level of specialty training.

The method according to the present invention accordingly provides for very simple and easy method for the rapid detection and quantification or target molecules, for example an environmental pollutant.

Aptamers

Specific to the present invention, is the provision of aptamers comprising the sequence: 5'-ATACGAGCTTGT-TCAATACGAAGGGATGCCGTTTGGGCCCAAGTTC GGCATAGTGTGGTGTAGTAAGAGCAATC-3'(SEQ ID NO: 1), or a sequence having 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity.

Specifically the aptamer is: $NH_2(CH_2)_6$ATACGAGCTT-GTTCAATACGAAGGGATGCCGTTTGGGCCCAAGT-TCGG CATAGTGTGGTGTAGTAAGAGCAATC-3' (SEQ ID NO: 1), or a sequence having 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity.

Abbreviations

BPA bisphenol A
BWB Binding and washing buffer: In this case, 2 mM TRIS—HCl, pH 7.5 containing 10 mM NaCl, 0.5 mM KCl, 0.2 mM $MgCl_2$, 0.1 mM $CaCl_2$, 5% v/v EtOH; 1% v/v IGEPAL® non-ionic surfactant
DLS Dynamic Light Scattering
$D_t$ particle diffusion coefficient
E2 17β-oestradiol
EDC 1-ethyl-3-(3-dimethylaminopropyl) carbodiimide
FWHM Full Width at Half Maximum
MES 2-(N-morpholino)ethanesulfonic acid
MP microparticle
IGEPAL® (Octylphenoxy)polyethoxyethanol
NHS N-hydroxysuccinimide
NP nanoparticle
PALS Phase Analysis Light Scattering
PTA Particle Tracking Analysis
ssDNA single strand DNA
RPS Resistive Pulse Sensing

EXAMPLES

Figure 1:
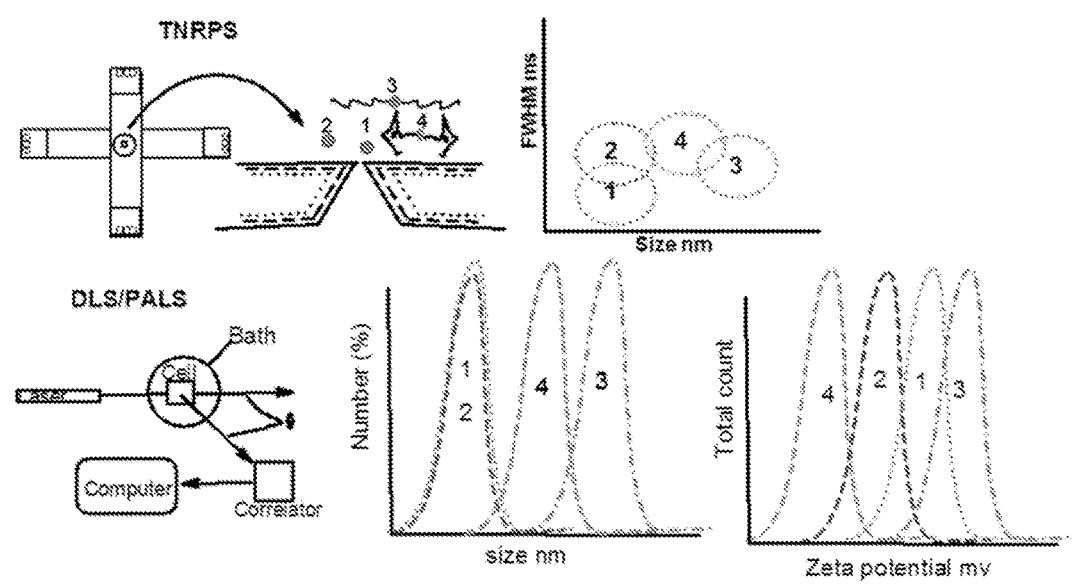
FIG. 1 shows a general schematic of the detection of NPs (1), Activated NPs (2), NPs-Aptamer (3) and NPs-Aptamer+ E2 by Light scattering and resistive pulse sensing.
Figure 2:
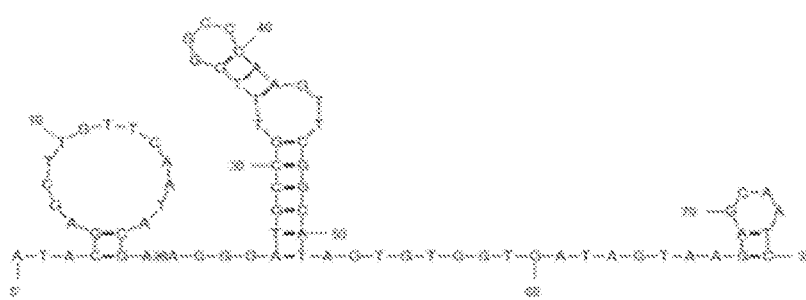
FIG. 2 shows the predicted secondary structure of the E2aptamer of formula (8) (SEQ ID NO: 1).
Figure 3:
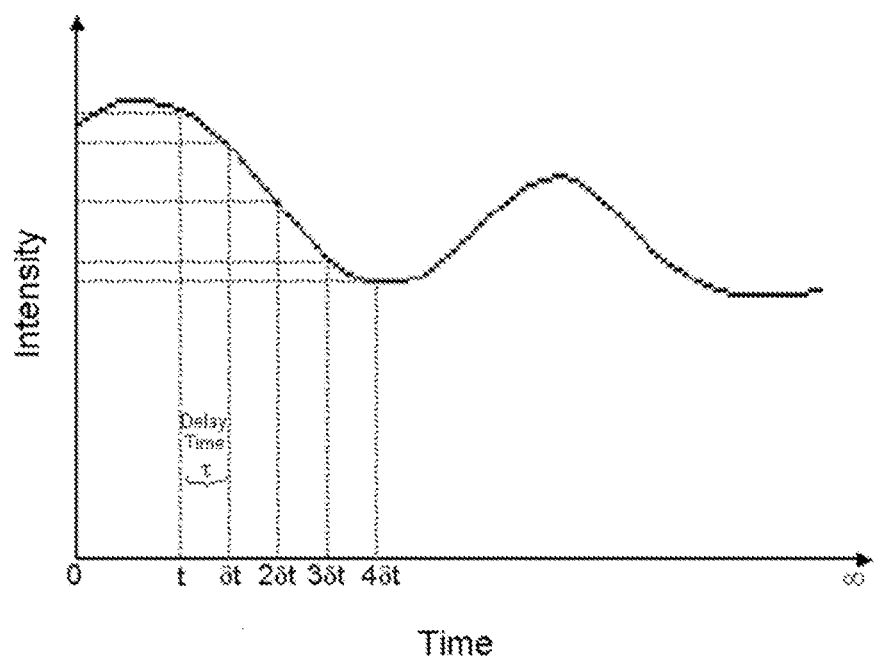
FIG. 3 shows intensity fluctuation of the scattered light by a sample containing the nanoparticle suspension.
Figure 4:
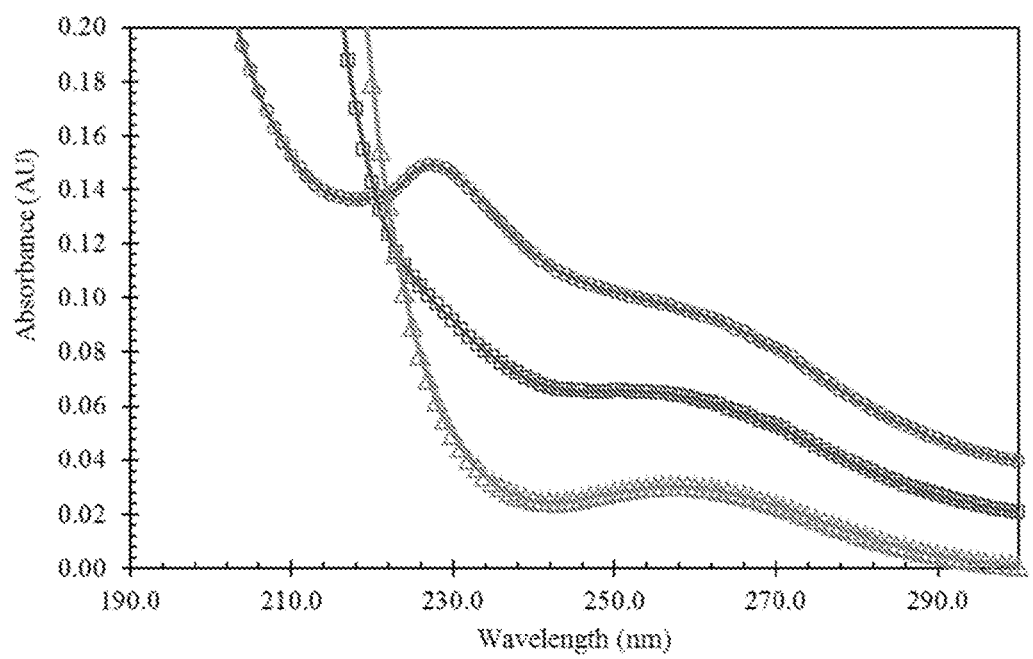
FIG. 4 shows UV absorption of NHS confirming the activation of carboxylated nanoparticles (1) to form (5). The samples were serially quenched at different reaction times (○=before reaction, □=after 20 minutes and Δ=after 1 hour. The reaction occurred between 6 nmole of EDC, NHS and 200 μL NPs (~4 nmole of COOH). The reactions were quenched by filtering the samples through 0.25 μm filters and measuring the absorption of the supernatant.
Figure 5:
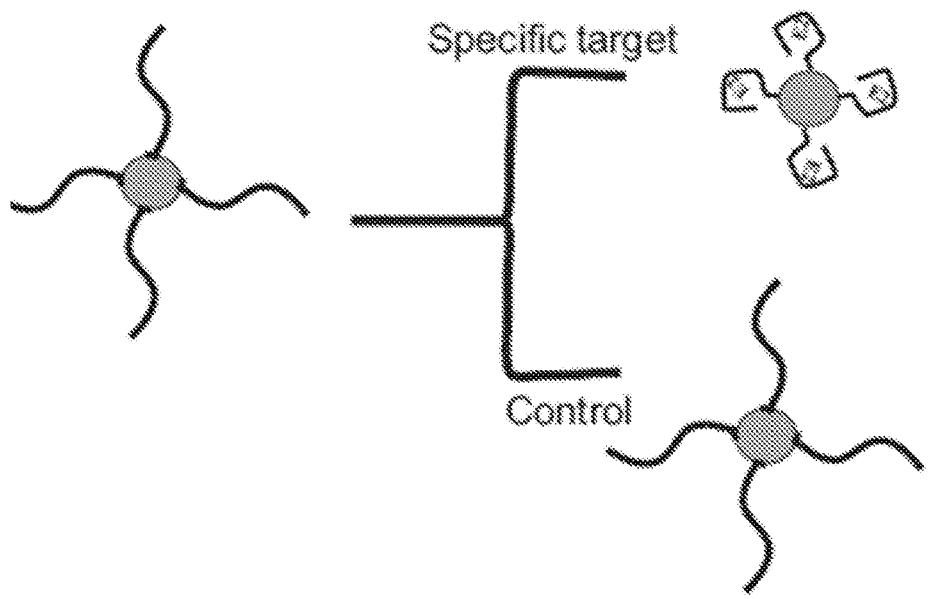
FIG. 5 shows a general schematic of the mechanism involved in the recognition of substrate E2 by the NP-E2aptamer conjugate.
Figure 6:
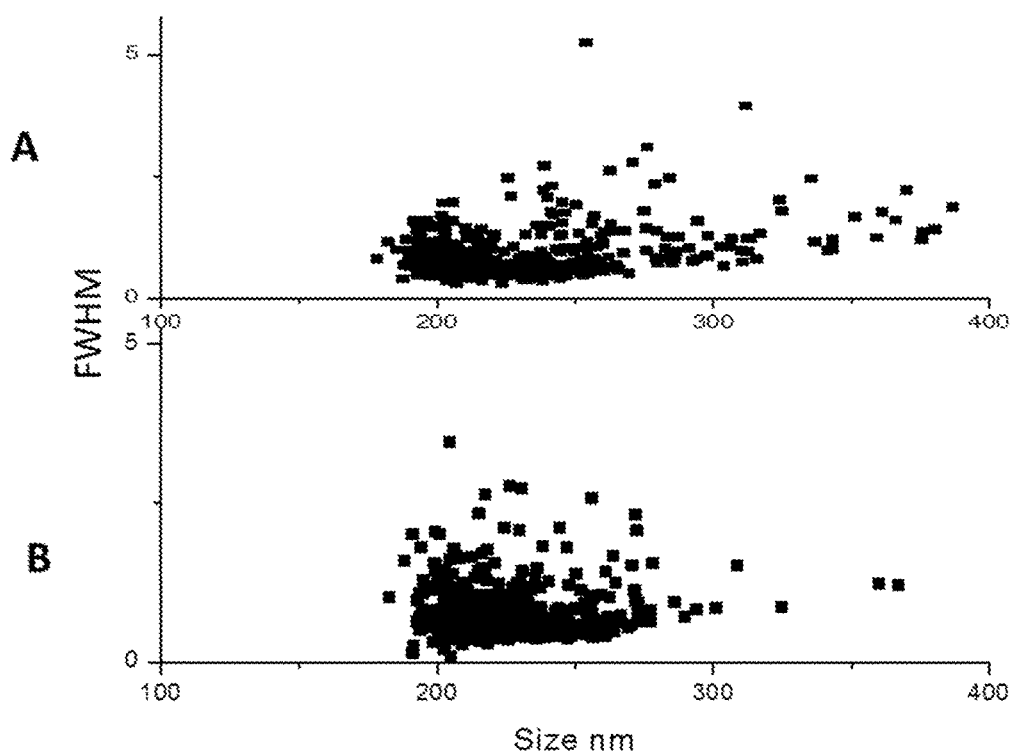
FIG. 6 shows a scatter plot of size and FWHM of a control experiment: (A) bare NPs and (B) bare NPs are reacted with 50 nM E2.
Figure 7:
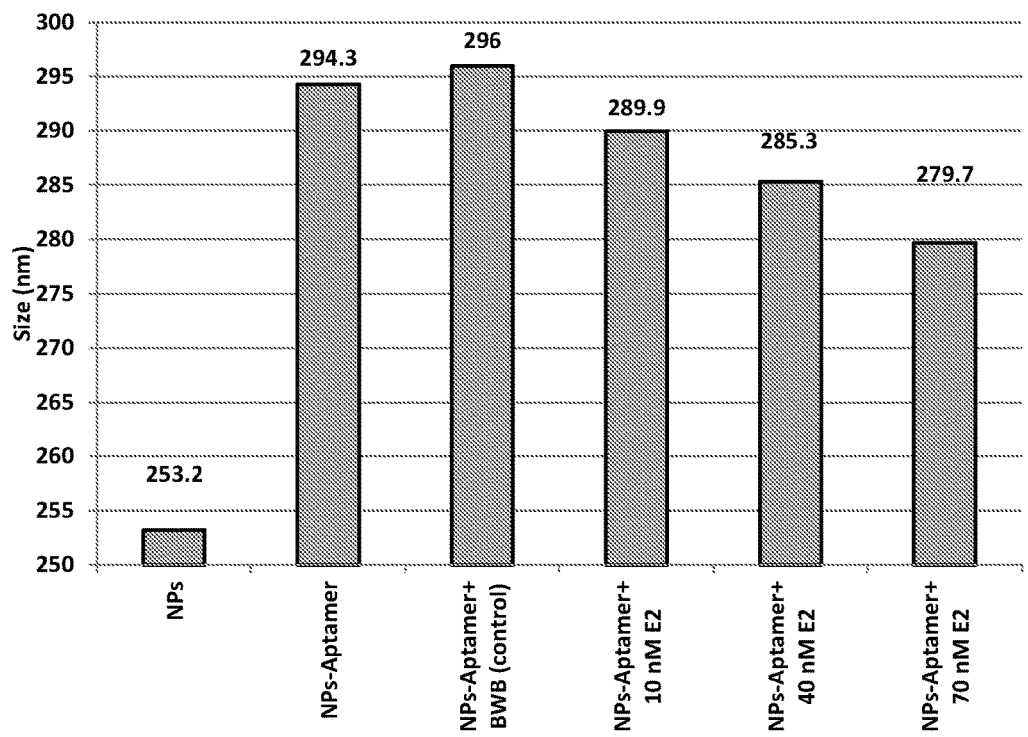
FIG. 7 show results obtained using DLS for the detection of 10 nM, 40 nM and 70 nM E2 using NP-E2aptamer conjugate. The detection was performed as described in Table 2 and subsequently diluted using the same buffer conditions to provide a total sample volume of 1 mL.
Figure 8:
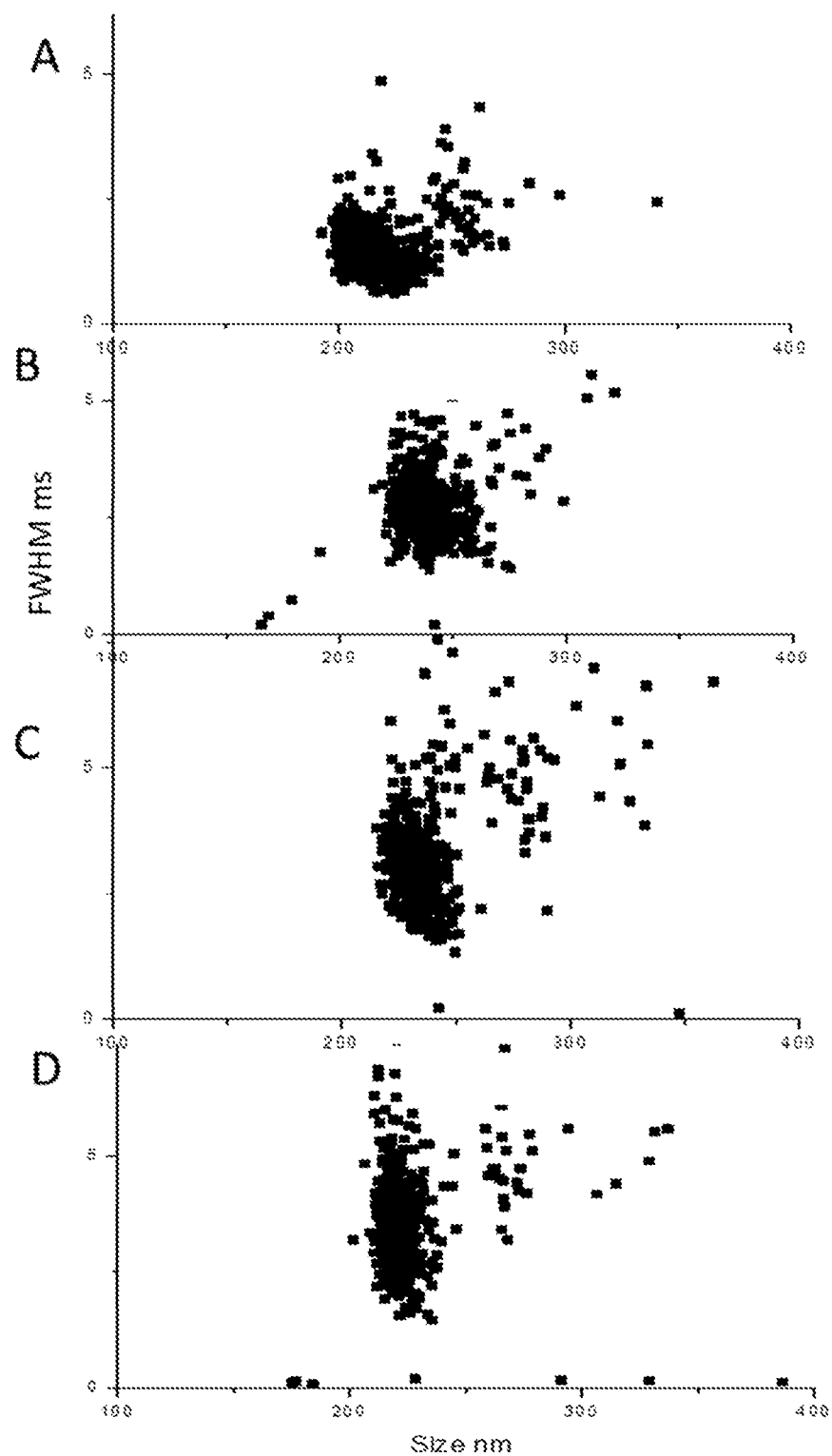
FIG. 8 shows scatter plot of (A) NPs, (B) NP-E2aptamer conjugate (7) and the detection of E2 at (C) 5 nM and (D) 20 nM at 0.1 aptamer density.

The examples described herein are for the purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention. The procedures below are described for the preparation of the NP-E2aptamer but are also suitable for use with other aptamers and are not limited to only the E2aptamer.

The PAGE purified $H_2$N-E2Aptamer is custom synthesised by SIGMA-ALDRICH using the oligonucleotide sequence that was provided by the inventors.

Compound (5)

Carboxylated nanoparticles (1) (400 µL, 1.76E14 particles $mL^{-1}$, corresponding to 8 nmole surface carboxylic acid groups; Bangs Labs) are suspended in 2-(N-morpholino)ethanesulfonic acid. Compound (5) is formed by adding 1-ethyl-3-(3-dimethylaminopropyl) carbodiimide (2) (200 nmole, 20 µL of 0.01 M in MES) and N-hydroxysuccinimide (4) (200 nmole, 20 µL of 0.01 M in MES) and incubating the reaction mixture for 30 minutes at room temperature. For characterization purposes, compound (5) was isolated by centrifuging at 14,000 rpm for 20 minutes.

The formation of compound (5) with varying surface activation density is monitored in a separate series of reactions by reacting (1) with 1.5 equivalents of (2) and (4) so that the consumption of NHS can be monitored by UV absorption. Carboxylated nanoparticles (1) (200 µL, 1.76E14 particles $mL^{-1}$, corresponding to 4 nmole surface carboxylic acid groups; Bangs Labs) are suspended in 2-(N-morpholino)ethanesulfonic acid in five separate reaction vessels. 1-ethyl-3-(3-dimethylaminopropyl) carbodiimide (6 nmole, 100 µL of 50 µM in MES) and N-hydroxysuccinimide (6 nmole, 100 µL of 50 µM in MES) are added to each of the five reaction vessels at room temperature. The five reactions are quenched after 5, 10, 20, 30, and 60 minutes, respectively, by filtering through a 0.2 µm syringe filter and the consumption of NHS is monitored by measuring the UV absorption of the supernatant liquid.

Coupling of the $H_2$N-Aptamer (6) to (5) to Form the NP-Aptamer Conjugate (7)

Carboxylated nanoparticles (1) (400 µL, 1.76E14 particles $mL^{-1}$, corresponding to 8 nmole surface carboxylic acid groups; Bangs Labs) are suspended in 2-(N-morpholino)ethanesulfonic acid. Compound (5) is formed by adding 1-ethyl-3-(3-dimethylaminopropyl) carbodiimide (2) (200 nmole, 20 µL of 0.01 M in MES) and N-hydroxysuccinimide (4) (200 nmole, 20 µL of 0.01 M in MES) and incubating the reaction mixture for 30 minutes at room temperature. After 30 minutes, 0.2 nmole of amino terminated E2aptamer (160 µL of 650 nM in MES) is then added to the reaction mixture and incubated a room temperature overnight. The NP-E2aptamer conjugate (7) is then isolated for further experiments by centrifuging at 14,000 rpm for at least 20 minutes. The example described here for the generation of compound (7) results in an average of approximately 1000 aptamer probes per nanoparticle.

The success of tethering can be ascertained by measuring the zeta potential of NPs after isolation via centrifuging and re-dispersion in MES buffer. Table 2 shows that the formation of the (neutral) NHS ester is confirmed via a reduction in zeta potential to −32 mV compared with −36 mV for the bare NPs which have an anionic carboxylate surface. The zeta potential of the NPs then increases to −41 mV upon coupling the polyanionic aptamer. These observations reflect a covalent functionalization rather than non-specific adherence to the NP surfaces because the bare NP zeta potential is obtained when the coupling agents are omitted. The density of aptamer functionalization is estimated at approximately $2.4 \times 10^3$ aptamers per particle (corresponding to a mean surface area of ~25 $nm^2$ per aptamer) by measuring the coupled aptamer concentration when a fluorescently tagged aptamer is used. By measuring the degree of coupling as a function of the NP:aptamer concentration ratio in the coupling reaction, it is found that this density of functionalization corresponds to the saturated value.

TABLE 2

Absolute values of zeta potential obtained via phase analysis light scattering for populations generated during the coupling of E2aptamers to NPs and during the detection of E2.

| Samples | Zeta Potential[a]/mV in MES buffer | Zeta Potential[a]/mV in BWB buffer |
|---|---|---|
| NPs | −36.0 (0.1) | −32.5 (1.0) |
| NP-NHS | −32.3 (2.0) | Not measured |
| NPs + aptamer no EDC/NHS | −36.0 (0.8) | Not measured |
| NP-aptamer | −41.3 (0.6) | −33.5 (0.5) |
| NPs + 50 nM E2 | Not measured | −32.0 (1.0) |
| NP-aptamer + 50 nM E2 | Not measured | −28.2 (0.5) |

[a]values in parentheses indicate standard deviation over three samples

Figure 17:
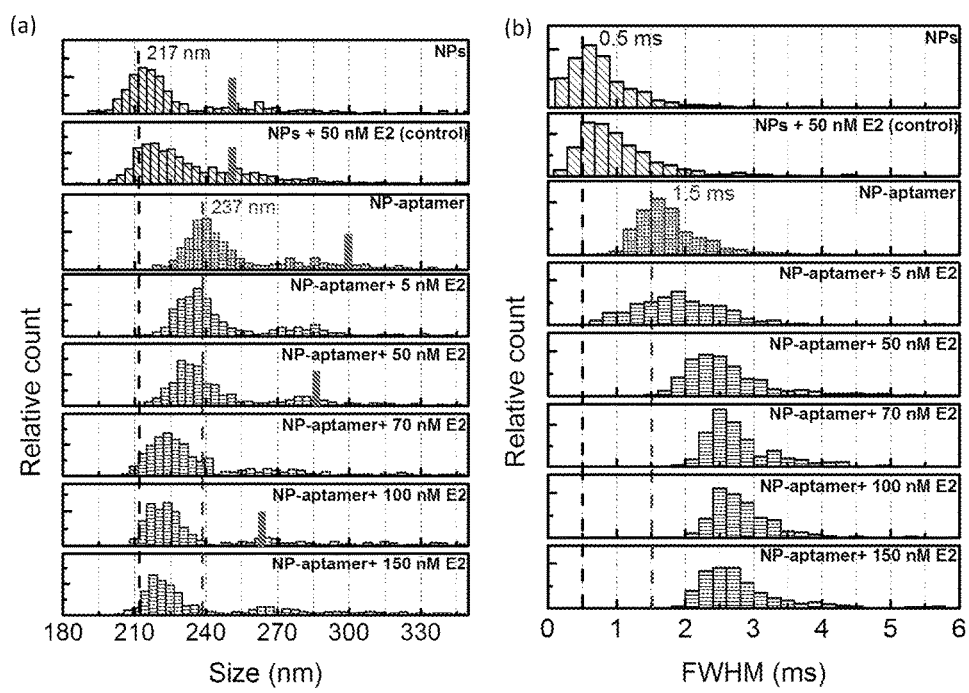
FIG. 17: (A) shows histograms of the size of the NP-E2aptamer-substrate conjugate at different concentrations obtained by TRPS during the detection process of E2. The locations of solid bins indicate the averages of size distributions by number obtained from DLS; (B) shows FWHM histograms of the size of the NP-E2aptamer-substrate conjugate obtained by TRPS during the detection process of E2. The dashed vertical lines are aligned to the mode bars of the bare NPs and NP-E2aptamer. The bin sizes are 3.5 nm and 0.2 ms for size and duration (FWHM) respectively.

FIG. 17(A) exemplifies that TRPS resolves an approximately 20 nm increase in the mode diameter of NPs as a result of coupling aptamers. It is apparent that, although DLS and TRPS measurements reveal the same trend, the absolute diameters differ. This is not unexpected, because DLS gives an average based on a number distribution which is derived from the intensity distribution of scattered light, whereas TRPS number distributions are based upon particle-by-particle measurements.

Detection of E2

100 µL of test solution are prepared by combining NP-aptamer conjugate (7) (90 µL of stock solution 5.2E10 NPs $mL^{-1}$) in BWB with aliquots of E2 in BWB as shown in Table 3 below to obtain test solutions providing E2 concentrations of 5 nM and 20 nM respectively. The samples are incubated for 20 minutes at room temperature and sonicated for 3-5 minutes before analysis using RPS.

TABLE 3

Recipes of the detection samples

| Final conc. E2 | Vol. compound (7) (5.2E10 NPs mL$^{-1}$) in BWB | Vol. E2 stock (0.5 µM) in BWB | Final vol. made up with BWB | Incubation time, temperature |
|---|---|---|---|---|
| 0M (control) | 90 µL | 0 µL | 100 µL | 20 min, RT |
| 5 nM | 90 µL | 1 µL | 100 µL | 20 min, RT |
| 20 nM | 90 µL | 4 µL | 100 µL | 20 min, RT |

Experimental Results on the Effect of Detergent

Figure 12:
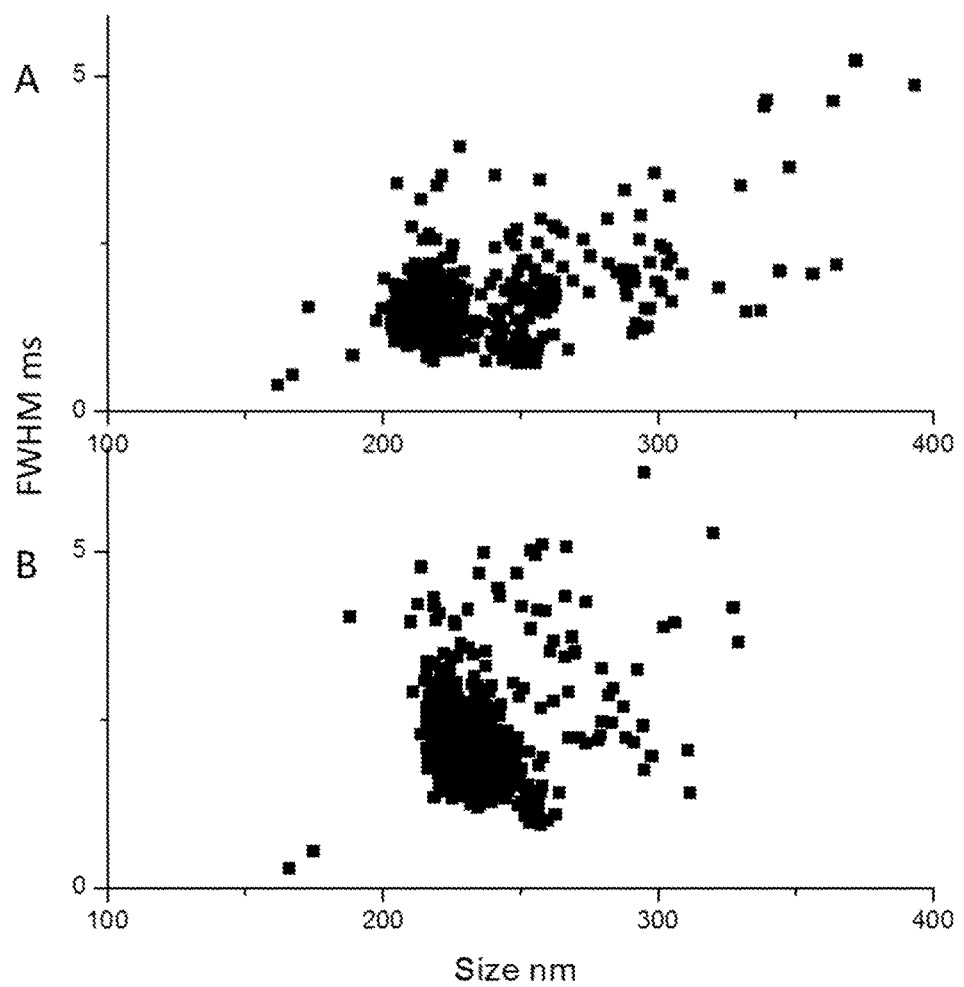
FIG. 12: (A) represents NP-E2aptamer conjugate in BWB, 0.01% IGEPAL™; (B) represents NP-E2aptamer conjugate in BWB, 0.1% IGEPAL™.
Figure 13:
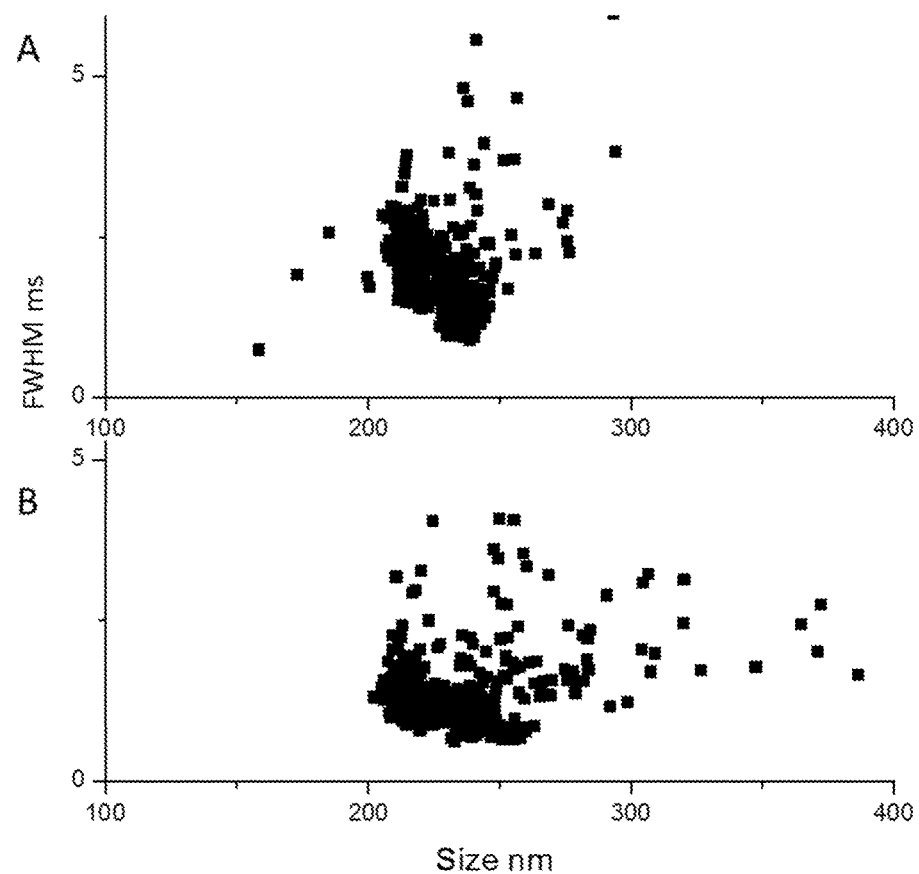
FIG. 13: (A) represents NP in BWB, 0.01% IGEPAL™ (B) Represents NP in BWB, 0.1% IGEPAL™.
Figure 14:
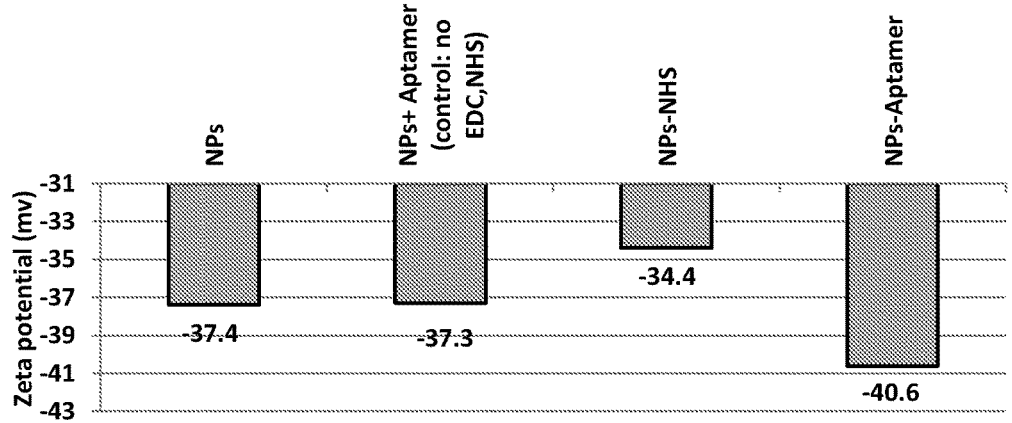
FIG. 14 shows surface potential (specifically ζ-potential) measurements of NPs, NPs-NHS conjugate (5) and NP-E2aptamer conjugate (7).
Figure 15:
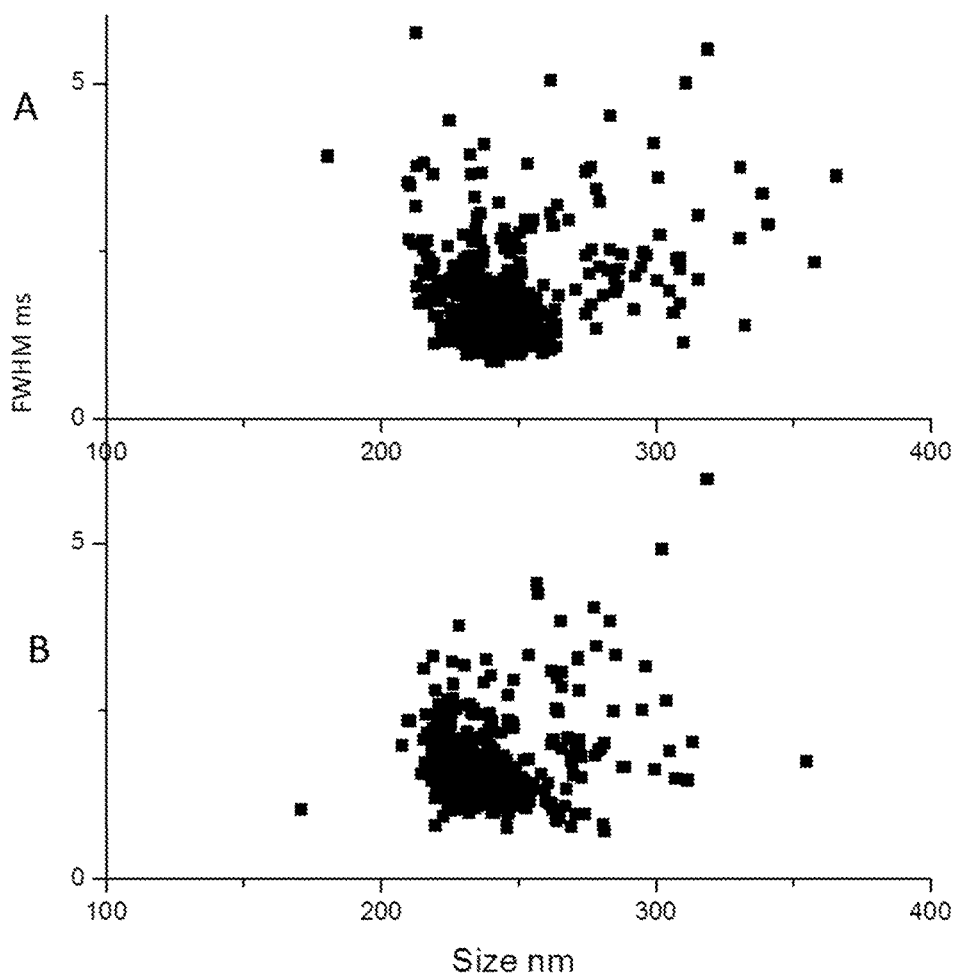
FIG. 15 shows scatter plot of a control sample NP-E2aptamer conjugate (7) and NP-E2aptamer conjugate (7) together with BWB.
Figure 16:
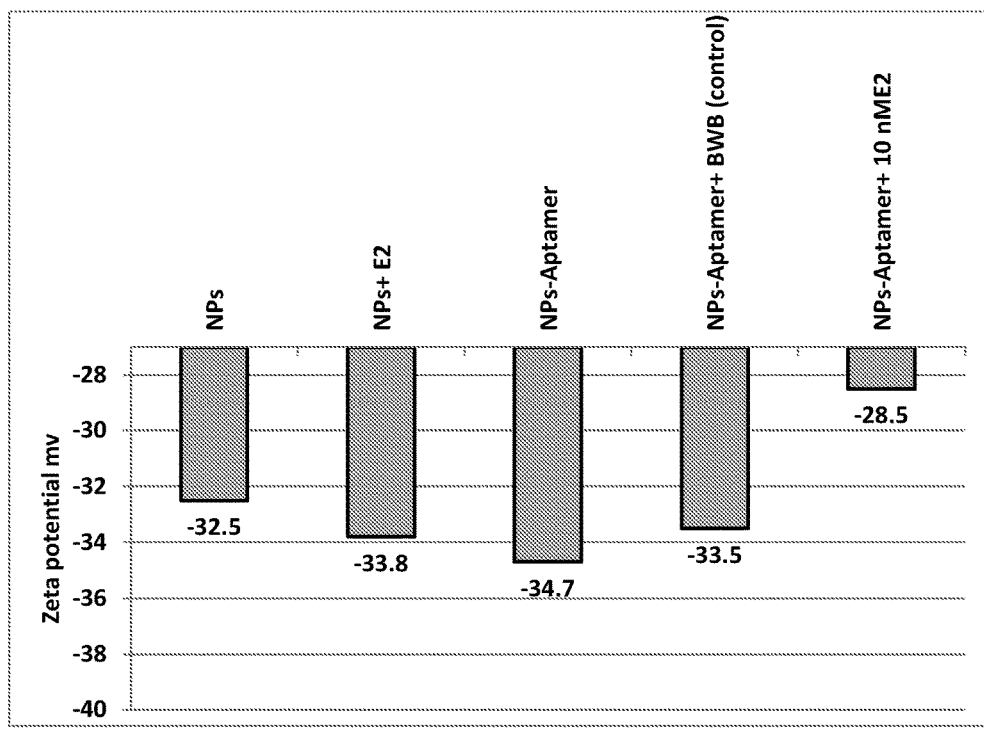
FIG. 16 shows surface potential (specifically ζ-potential) measurements of NPs, NP-aptamer conjugate and NP-E2aptamer-substrate conjugate at 10 nM E2.

NPs and NP-aptamer conjugate (7) (5.2E10 particles mL$^{-1}$) are suspended in BWB with different amount of IGEPAL® detergent (0.1% v/v and 0.01% v/v) and the analysed by RPS, DLS ζ-potential via PALS as shown in FIG. 12A and FIG. 12B. Aside from the variation in detergent concentration, the same procedure outlined above for the control in the sensing measurements is followed.

Detection of Other Small Molecules Using the E2 Aptamer

Figure 22:
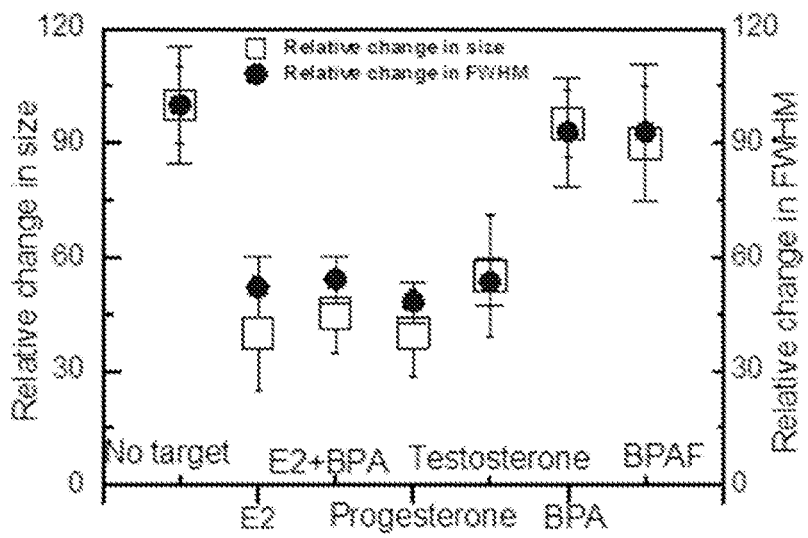
FIG. 22 shows changes in the mode values of size and FWHM obtained by TRPS during the specificity examination of 50 nM of E2, BPA+BPA, progesterone, testosterone, Bisphenol A and Bis (4-hydroxyphenyl) methane (error bars indicate the standard deviation of the average from three independent measurements). Relative change in size was calculated from the 20 nm extension of aptamer added to NPs and relative change in FWHM duration was calculated from the duration of NP-aptamer (1.5 ms).
Figure 23:
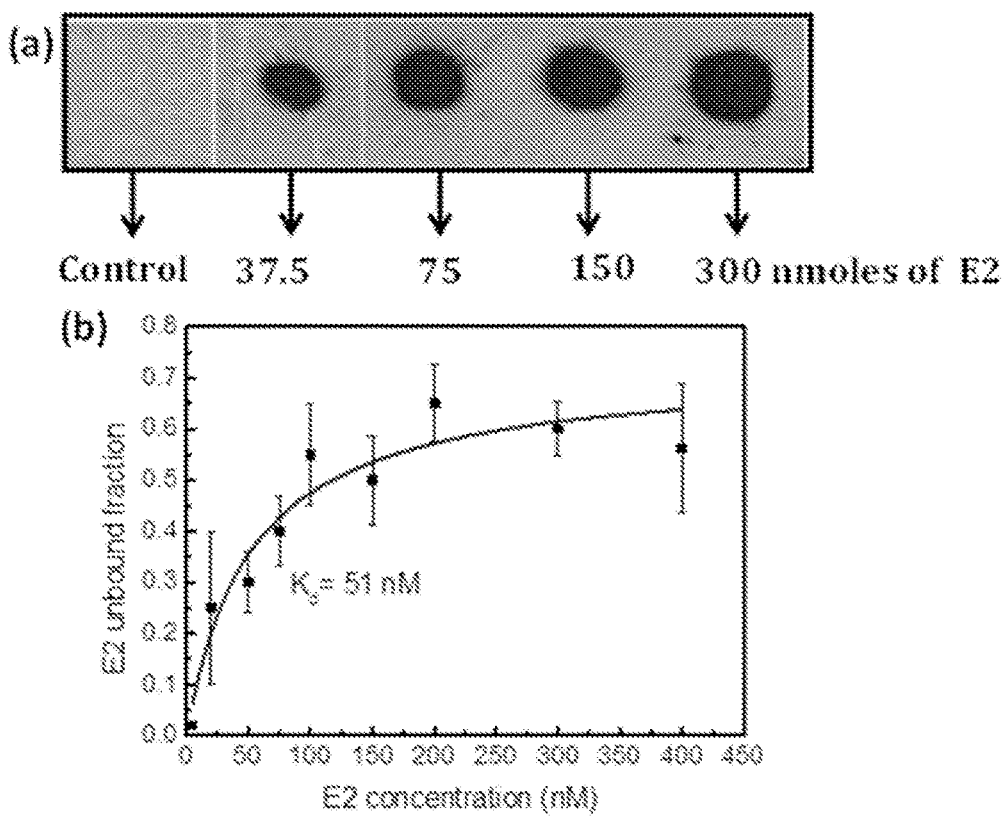
FIG. 23: (A) shows dot blot detection of serial amounts of immobilised E2 on nitrocellulose and chemoluminescence visualisation of E2 bound to the NP-aptamer conjugate; (B) shows the determination of the dissociation constant using NP-aptamer conjugate, and measurement of the E2 fluorescence in the supernatant samples after incubation. NP-aptamer concentration is 100 nM (error bars indicate the standard deviation of the mean of three independent experiments).

The specificity of a NP-E2aptamer conjugate is investigated for other target molecules. Experiments are performed using the same conditions as noted above for the detection of E2. FIG. 22 shows that this particular NP-E2aptamer conjugate does not distinguish between E2, progesterone and testosterone which are classified in the same steroidal family. However, excellent discrimination is achieved against molecules that do not belong to the steroidal family, for example Bisphenol A and Bis (4-hydroxyphenyl) methane. This is an example indicating that NP-E2aptamer conjugates can be developed to be specific for a class of molecules belonging to the steroidal family which can be an advantage when related target molecules may trigger the same adverse effect and can be treated as single target. However, this example does not imply that NP-E2aptamer conjugates cannot be generated to target specific classes of steroidal molecules such as oestrogens.

Detection of Adenosine

Figure 9:
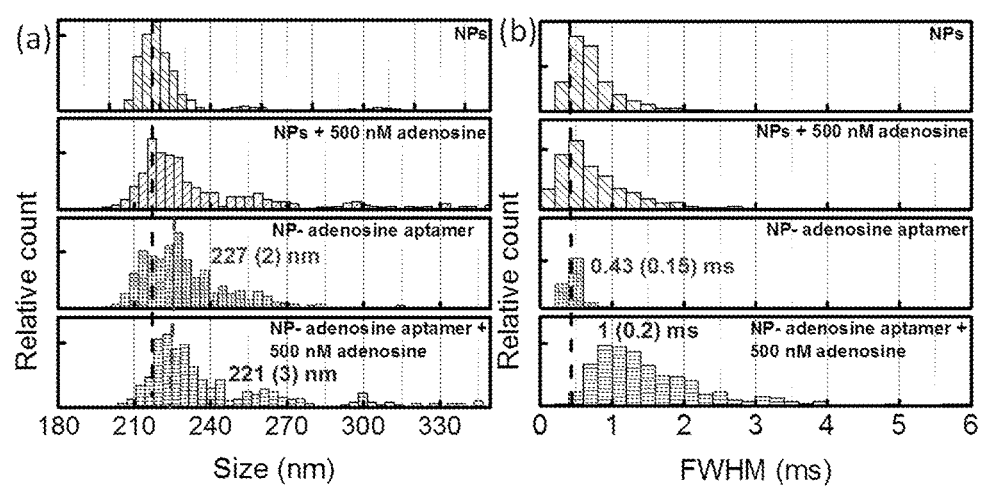
FIG. 9: (A) shows size histograms of different samples obtained by TRPS during the detection of 500 nM adenosine; (B) shows FWHM histograms of different samples obtained by TRPS for detection of 500 nM adenosine. The dashed vertical lines are aligned to the mode bars of the bare NPs (top [first] histogram) and NP-aptamer (third histogram). The bin sizes are 3.5 nm and 0.2 ms for size and duration (FWHM), respectively. Numbers in parentheses indicate the standard deviation of the mean of three measurements.
Figure 10:
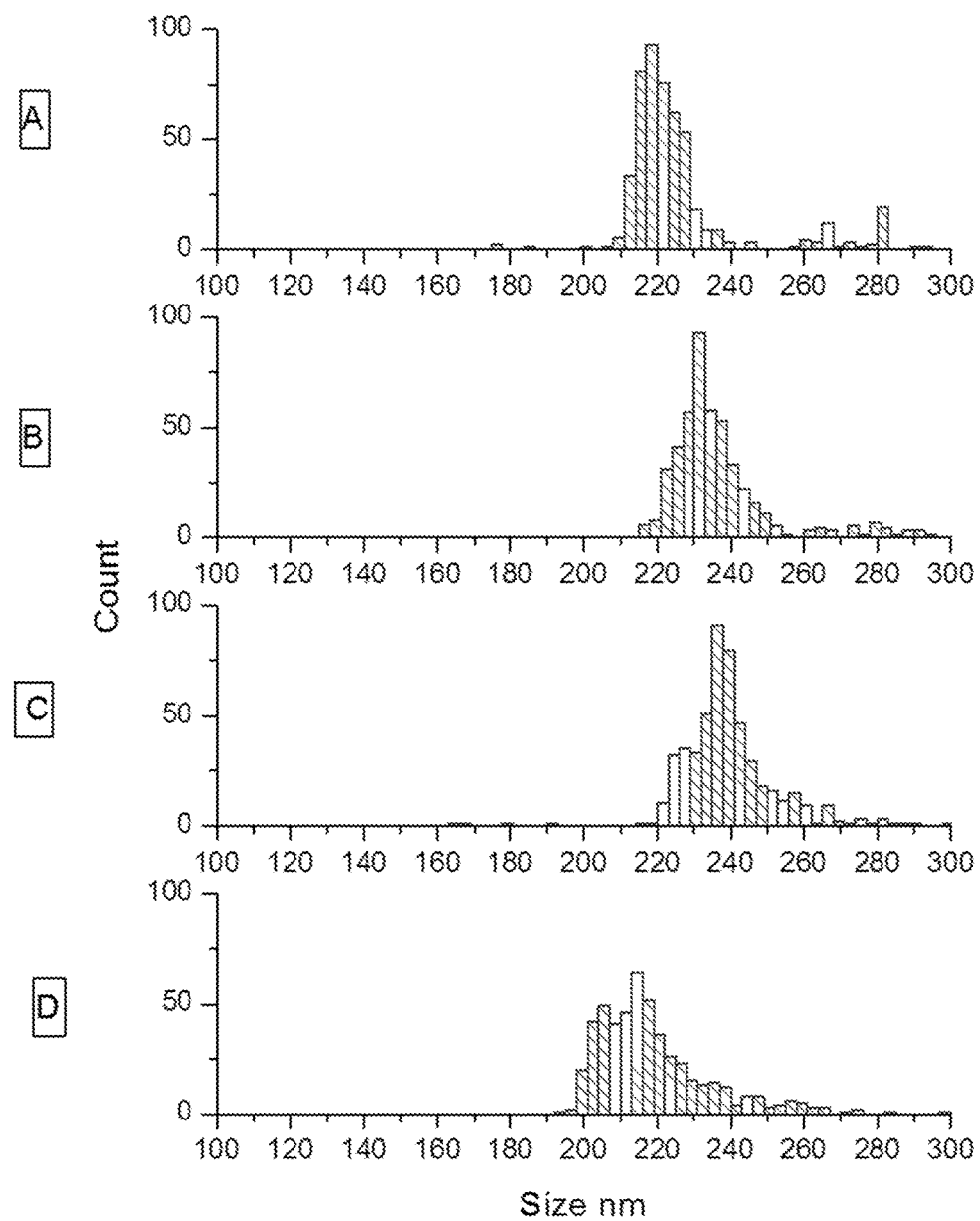
FIG. 10: (A) is a histogram of the size of NP-E2aptamer-substrate conjugate at a concentration of 20 nM E2; (B) is a histogram of the size of NP-E2aptamer-substrate conjugate at a concentration of 5 nM E2; (C) is a histogram of the size of NP-E2aptamer conjugate (7); (D) is a histogram of the size of NP (1).
Figure 11:
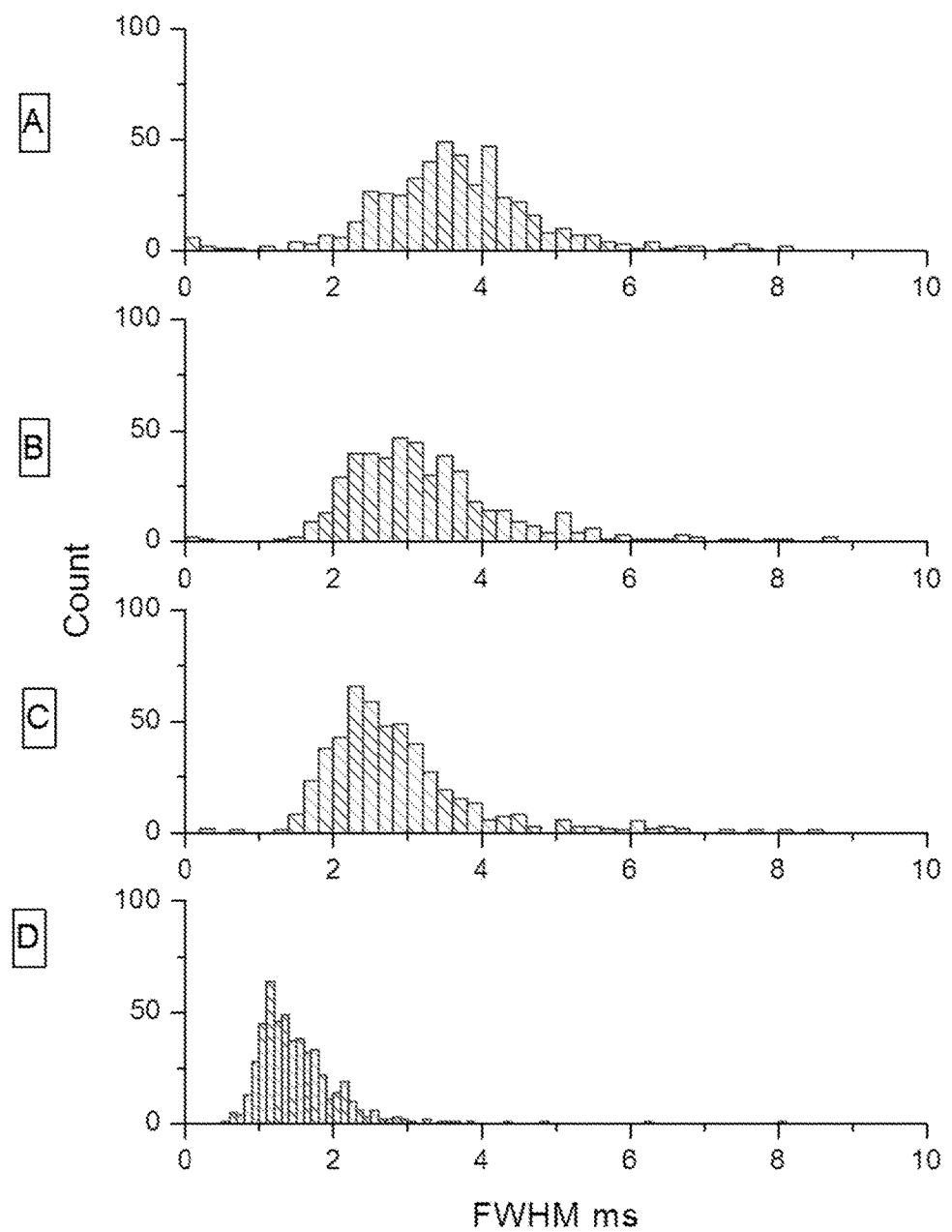
FIG. 11: (A) is a histogram of FWHM of NP-E2aptamer-substrate conjugate at a concentration of 20 nM E2; (B) is a histogram of FWHM of NP-E2aptamer-substrate conjugate at a concentration of 5 nM E2; (C) is a histogram of FWHM of NP-E2aptamer conjugate (7); (D) is a histogram of FWHM of NP (1).

The adenosine aptamer (Kim, J., Kim, I. Y., Choi, M. S., Wu, Q., Chem. Commun., 2009, 4747-9) is coupled to 217NP following the same protocol to couple the E2 aptamer to the NP (above). The bare NP shows an increase in Zeta potential from −36.0 to −40 mV, confirming that the coupling is successful. Approximately, 10 nm increase in diameter is observed using TRPS as shown in FIG. 9a. The increase in diameter is not associated with a change in the particle duration FWHM as shown in FIG. 9b. Without wishing to be bound by theory, it is postulated that the latter may be a balance between a steric drag effect and electrophoretic mobility. Adenosine is able to be detected, using the adenosine aptamer, under the same buffer and nanopore conditions applied for the detection of E2, at levels as low as 500 nM as shown in FIGS. 9a and 9b. The adenosine is detected by a decrease in NP-adenosine aptamer conjugate (from 227 to 221 nm) and an increase in the particle pulse duration FWHM (from 0.43 to 1 ms).

General Procedure for RPS Analysis of Samples

40 µL of the sample solution described in Table 2 is placed in the upper cell of RPS and 500 blockade events are recorded under a constant voltage and nanopore size. The BWB (used to make the sample solutions in Table 3 in the present example) is comprised of 2 mM TRIS—HCl, pH 7.5 containing 10 mM NaCl, 0.5 mM KCl, 0.2 mM MgCl$_2$, 0.1 mM CaCl$_2$, 5% v/v EtOH; 1% v/v IGEPAL™ non-ionic surfactant.

General Procedure for DLS Analysis of Samples

Samples for size measurements via DLS are prepared in the same way as for RPS, except that the 100 µL sample solutions detailed in Table 3 are subsequently diluted using the same buffer (BWB) to a total volume of 1 mL.

Samples for the measurements of ζ-potential via PALS for are prepared in the same way as for RPS, except that the 100 µL sample solutions detailed in Table 3 are subsequently diluted using deionised water to a total volume of 1 mL.

General Procedure for Tunable Resistive Pulse Sensing (TRPS)

Figure 18:
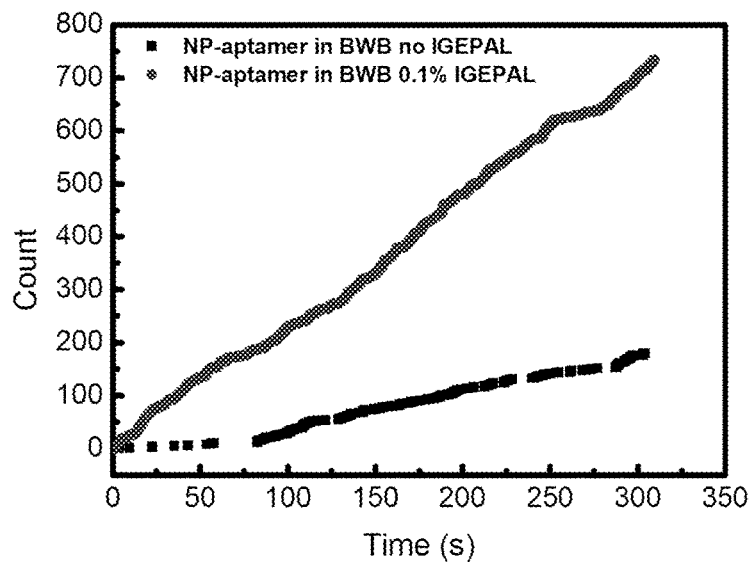
FIG. 18 shows the effect of IGEPAL on the NP-aptamer count rate in TRPS.

A tunable pore membrane (size designation NP200) is mounted on a qNano instrument, both obtained from Izon Science. The membrane is stretched until the desired pore size is reached, in this case with the teeth of the device separated by 46.11 mm. 0.754 BWB with no detergent is placed in the lower fluid cell and 40 µL BWB with 0.1% IGEPAL detergent is placed in the upper cell. The presence of IGEPAL in the BWB facilitates smooth NP-aptamer transit in TRPS (see FIG. 18). An external voltage of 0.26 V is applied between the electrodes in the upper and lower fluid cells to give a background current (I) of 70±10 nA. 40 µL of the test sample is placed in the upper fluid cell, ensuring that no bubbles are present. At least 500 blockade events are collected (which generally took 4-7 minutes) and analysed using proprietary event analysis software from Izon Science (v. 2.2). Sizes are calculated after calibration with an appropriate standard sample, typically the carboxylated polystyrene NPs with a diameter of 217 nm.

Figure 19:
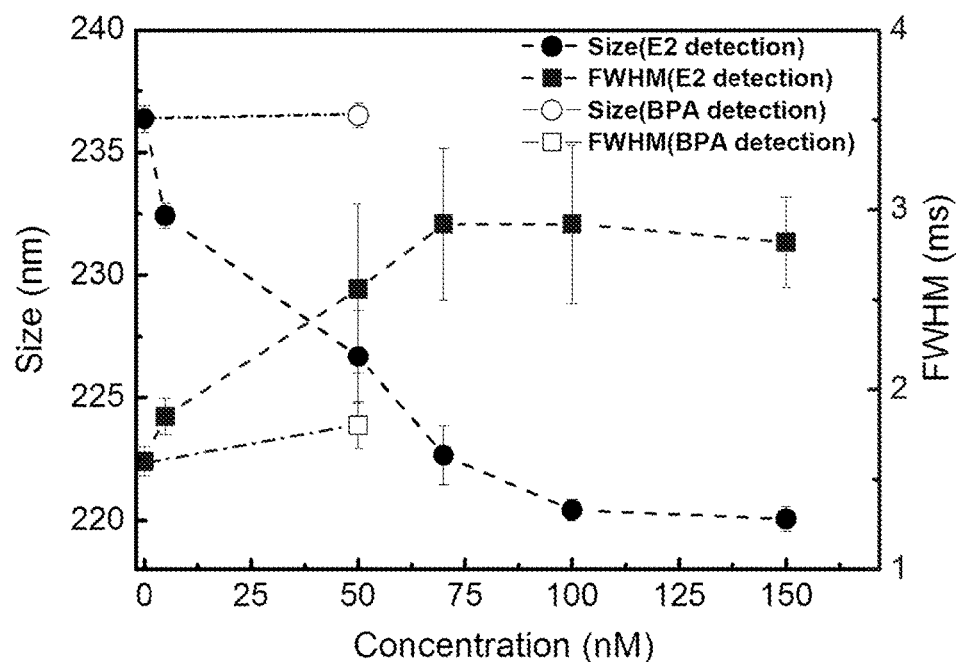
FIG. 19 shows mode values of size and FWHM obtained by TRPS during the detection of E2, and cross reactivity examination of bisphenol-A (BPA). Error bars indicate the standard deviation of the average from three independent experiments.

FIG. 19 shows that the TRPS method of E2 detection is remarkably robust and reproducible, with variation less than 5% and 20% for NP-aptamer size and pulse duration measurements (FWHM), respectively, for three independent experiments carried out starting from the functionalization of carboxylated NPs. FIG. 19 also illustrates the strong correlation that exists between NP-aptamer size and pulse duration measurements, confirming that both have a common origin. It is possible to reliably detect E2 at concentrations as low as 5 nM. FIG. 19 also shows excellent discrimination against the endocrine disrupting agent bisphenol-A (BPA) in a cross-reactivity experiment. Both the NP-aptamer size and pulse duration are statistically unaffected by the presence of 50 nM BPA.

General Procedure for Fluorescence

Fluorescence experiments using CY5.5 [(IUPAC name—1H-Benz[e]indolium, 2-[5-[3-[6-[(2,5-dioxo-1-pyrrolidinyl)oxy]-6-oxohexyl]-1,3-dihydro-1,1-dimethyl-6,8-disulfo-2H-benz[e]indol-2-ylidene]-1,3 pentadien-1-yl]-3-ethyl-1,1-dimethyl-6,8-disulfo-, inner salt, sodium salt (1:3)) as a fluorescent tag at the 3' end of the aptamer (reference: http://www.fluorophores.tugraz.at)] are performed using differing amounts of NPs ($1.04 \times 10^{10}$, $2.08 \times 10^{10}$, $3.12 \times 10^{10}$ and $4.16 \times 10^{10}$) in stock solution and the previously mentioned coupling reaction is applied using the fluorescently tagged aptamer (F-aptamer). After incubation and purification, the NP-aptamer samples are suspended in 500 µL MES buffer and the supernatant solutions are made up to 1 mL. The calibration curve is established by measuring the fluorescent intensity of different F-aptamer concentrations made in 500 µL MES buffer samples containing $2.08 \times 10^{10}$ particles mL$^{-1}$ of carboxylated NPs to account for any interference caused by scattering from the NPs. A standard 1 cm path length quartz fluorescence cell is used to measure the emission spectra over the wavelength range from 650 to 800 nm, with excitation at 645 nm. A 665 nm long pass filter is used to block scattered excitation light. The peak intensities at 700 nm are used for quantifying concentrations. Fluorescence experiments are performed with a Shimadzu RF-5301 PC spectrofluorophotometer. Excitation and emission slit widths are set to a resolution of 10 nm and 15 nm, respectively, in order to enhance the measured fluorescence intensities in such dilute samples.

Figure 20:
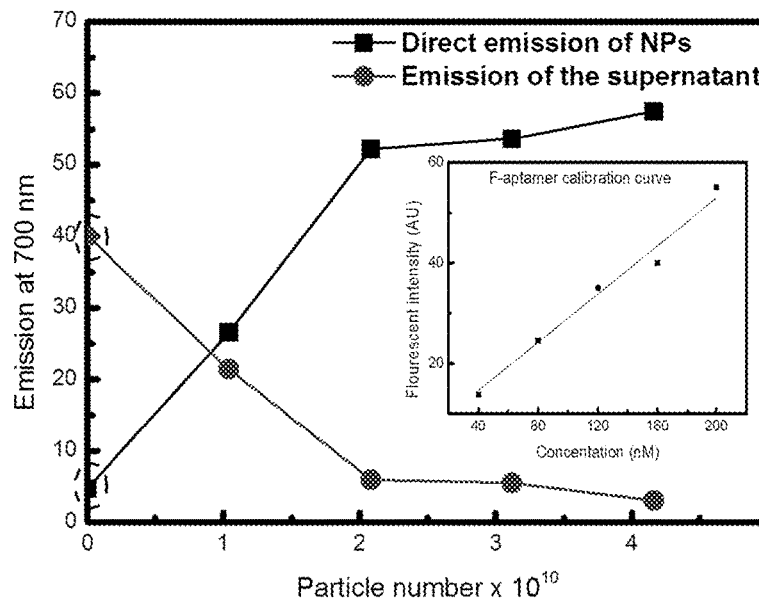
FIG. 20 shows fluorescence measurements of samples resulting from the reaction of several independent NP numbers ($1.04 \times 10^{10}$, $2.08 \times 10^{10}$, $3.12 \times 10^{10}$ and $4.16 \times 10^{10}$) with a fixed amount (0.1 nmol) of fluorescently tagged aptamer (F-aptamer). Dashed-circled data points represent the results of a control sample: exposure of $2.08 \times 10^{10}$ NPs to 0.1 nmol F-aptamer with no presence of the activating agents (EDC/NHS). The figure-inset is a calibration curve constructed of serial concentrations of the F-aptamer mixed with NPs ($2.08 \times 10^{10}$ particles).
Figure 21:
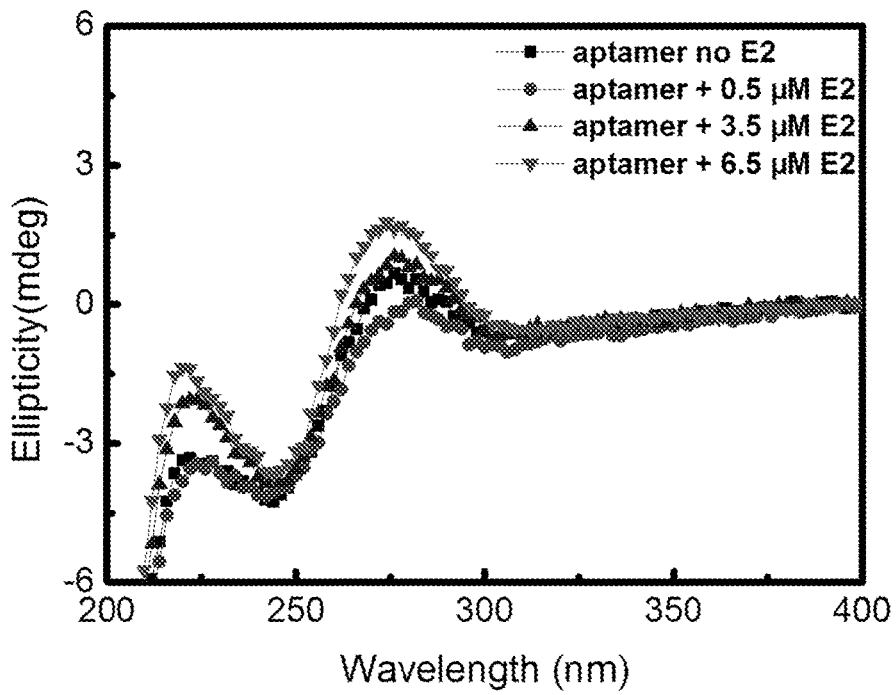
FIG. 21 is the CD spectra of 400 nM E2 aptamer in BWB and the independent detection of 0.5, 3.5 and 6.5 µM concentrations of E2.

FIG. 20 shows fluorescence measurements of samples resulting from the reaction of several independent NP numbers ($1.04 \times 10^{10}$, $2.08 \times 10^{10}$, $3.12 \times 10^{10}$ and $4.16 \times 10^{10}$) with a fixed amount (0.1 nmol) of fluorescently tagged aptamer (F-aptamer). Dashed-circled data points represent the results of a control sample: exposure of $2.08 \times 10^{10}$ NPs to 0.1 nmol F-aptamer with no presence of the activating agents (EDC/NHS).

The NPs used have carboxyl groups on their surface, 5 nmol of carboxylates for a particle number of $1.04 \times 10^{10}$ as determined by the manufacturer. Several amounts of NP—$1.04 \times 10^{10}$, $2.08 \times 10^{10}$, $3.12 \times 10^{10}$ and $4.16 \times 10^{10}$ are exposed to a fixed amount of F-aptamer (0.1 nmol), then the NP-F-aptamer conjugates are separated from the mixture when the coupling is finished as described herein, and the fluorescence is measured in both NP-F-aptamer and the supernatant samples.

As shown in FIG. 20, the fluorescent measurements result from a covalent functionalization and not non-specific adherence to the NP surfaces because the exposure of NPs ($2.08 \times 10^{10}$) to F-aptamer without activating agents (EDC/NHS) resulted in no interaction. The 0.1 nmol of F-aptamer is completely consumed by the second amount of NPs ($2.08 \times 10^{10}$) and the remaining amounts of NPs gave approximately the same fluorescent signal as shown in FIG. 20. This shows that the lower NP concentrations have a sufficiently high number of F-aptamer:NP ratio to saturate the NP surfaces, whereas the aptamers are coupled at lower density as the NP concentration is increased.

The fluorescent intensities of $1.04 \times 10^{10}$ and $2.08 \times 10^{10}$ samples are converted to concentrations and eventually number of nmol using a standard calibration curve constructed of several concentrations of F-aptamer mixed with $2.08 \times 10^{10}$ NPs. It is found that the number of F-aptamers per particle is $2.66 \times 10^3$, $2.6 \times 10^3$, $1.7 \times 10^3$ and $2.66 \times 10^3$ corresponding to the measurements in the samples containing $1.04 \times 10^{10}$ and $2.08 \times 10^{10}$ particles and their supernatant respectively. The overall average F-aptamer density is $2.4 \times 10^3$ per particle (standard deviation $0.4 \times 10^3$, n=4) giving 25 nm² free space for each aptamer. There is an additional uncertainty of approximately 11% from the lost NPs during the centrifuging process.

Circular Dichromism (CD)

Conformational transition studies by the CD technique are undertaken using a Chirascan CD spectrometer instrument. 1 mL of 400 nM solutions of E2 aptamer are made in BWB and independently contained different concentrations of E2 (0, 0.5, 3.5 and 6.5 µM). A standard 1 cm path length quartz cell is used to measure the CD spectra over the wavelength range from 200 to 400 nm and the scanning speed is 200 nm per minute.

Procedure for Dot Blotting Experiments

Nitrocellulose membranes are immersed in BWB for 10 minutes before drying. E2 is dissolved in ethanol (e.g. stock solution of 50 mg of E2 per milliliter of ethanol), spotted onto the membranes and then immersed in blotto blocking solution for 2 hours at room temperature. Biotin-labelled E2aptamer (3.16 µM in BWB) is incubated individually with the membranes containing different amounts of E2 overnight at 4° C. on a rocking incubator (15 oscillations/min). Non-specifically bound aptamers are removed by rinsing the membranes three times with BWB (10 minutes on a rocking incubator 40 oscillations/min). The bound substrate-aptamer conjugates are visualised using chemoluminescence by incubation with streptavidin-peroxidase conjugate (167 ng/mL in BWB). The incubation is left for 2 hours at room temperature. The washing of the aptamer is repeated using BWB to remove non-specifically bound streptavidin-peroxidase conjugate from the surface of the membranes. Chemoluminescence reaction solution for visualisation (0.1 M Tris-HCl pH 8.5, 25 µM luminal, 396 µM p-coumaric acid, and 0.01% of hydrogen peroxide in deionised $H_2O$), is prepared immediately before use. Membranes are incubated in the chemoluminescence solution for 1 minute at room temperature in a darkroom and then immediately placed on a clear plastic backing, wrapped using clear plastic wrap and placed in an x-ray cassette. X-ray films are carefully placed on top of the membranes and exposed for 15 minutes. The films are developed by soaking twice in GBX developing solution for 3 minutes and rinsed with deionised $H_2O$ between soaking.

We claim:

1. A method for the detection of 17-β estradiol in a sample comprising the steps:
    a) coupling a nanoparticle (NP) or microparticle (MP) to an aptamer specific for 17-β estradiol to form a NP-aptamer conjugate, wherein the aptamer comprises the sequence of SEQ ID NO: 1 or a sequence having at least 90% identity to SEQ ID NO: 1 and having selectivity for 17-β estradiol;
    b) contacting the NP-aptamer conjugate with the sample; and
    c) detecting a reduction in the size, a change in surface potential, or a change in mobility of the NP-aptamer conjugate, wherein the reduction or change is indicative of the presence of 17-β estradiol.

2. The method according to claim 1, wherein step (a) optionally comprises the step of detecting any reduction in the size, a change in surface potential, and/or a change in mobility of the NP-aptamer conjugate to ensure the aptamer has coupled to the NP or MP.

3. The method according to any one of claim 1, wherein the reduction in the size, a change in surface potential, and/or a change in mobility of the NP-aptamer conjugate is detected by a technique selected from RPS, DLS and combinations thereof.

4. The method according to any one of claim 1, wherein a detergent or surfactant, or combinations thereof, are used in step (b).

5. The method according to claim 4, wherein the detergent or surfactant is selected from an anionic surfactant or detergent, a cationic surfactant or detergent and non-ionic surfactant or detergent.

6. The method according to any one of claim 1, wherein the aptamer may comprise a fluorescent tag.

7. The method according to any one of claim 1, wherein the nanoparticle or microparticle is a size of about 5 nm to about 5 microns.

8. The method according to any one of claim 1, wherein the nanoparticle or microparticle is selected from the group consisting of gold, palladium, polystyrene, and latex.

9. The method according to any one of claim 1, wherein the NP or MP and aptamer are present in a ratio of about 1:1,000,000 to about 1:1, of the number of NP or MP to aptamer.

10. The method according to any one of claim 1, wherein the sample is an environmental sample or a biological sample.

11. The method according to claim 10, wherein the biological sample is an ex vivo biological sample.

12. A biosensor comprising:
(a) a nanoparticle or microparticle and;
(b) an aptamer comprising the nucleotide sequence ATACGAGCTTGTTCAATACGAAGGGATGC-CGTTTGGGCCCAAGTTCGGCATAGTGTGG TGATAGTAAGAGCAATC-3' (SEQ ID NO: 1) or a continuous sequence having 90, 91, 92, 93, 94, 95, 96, 97, 98, or 99% identity to SEQ ID NO: 1 and having selectivity for 17β-estradiol,
wherein the nanoparticle or microparticle is coupled to the aptamer to provide a NP-aptamer conjugate, and
wherein there is a reduction in the size, a change in surface potential, and/or a change in mobility of the NP-aptamer conjugate when the NP-aptamer conjugate is contacted with 17β-estradiol in a sample.

13. The biosensor according to claim 12, wherein the reduction in the size, a change in surface potential, and/or a change in mobility of the NP-aptamer conjugate is detected by a technique selected from RPS, DLS and combinations thereof.

14. The biosensor according to claim 12, comprising a detergent or surfactant, or combinations thereof.

15. The biosensor according to claim 14, wherein the detergent or surfactant is selected from an anionic surfactant or detergent, a cationic surfactant or detergent and non-ionic surfactant or detergent.

16. The biosensor according to claim 12, wherein the aptamer comprises a fluorescent tag.

17. The biosensor according to claim 12, wherein the nanoparticle or microparticle is a size of about 5 nm to about 5 microns.

18. The biosensor according to claim 12, wherein the nanoparticle or microparticle is selected from gold, palladium, polystyrene, and latex.

19. The biosensor according to claim 12, wherein the ratio of the number of NP or MP to aptamer is from about 1:1,000,000 to about 1:1.

20. The biosensor according to claim 12, wherein the sample is an environmental sample or a biological sample.

21. The biosensor according to claim 20, wherein the biological sample is an ex vivo biological sample.

22. The biosensor according to claim 12, wherein the aptamer comprises the sequence: 5'-ATACGAGCTTGT-TCAATACGAAGGGATGCCGTTTGGGCCCAAGT-TCGGC ATAGTGTGGTGATAGTAAGAGCAATC-3' (SEQ ID NO: 1).

23. An aptamer comprising the sequence: 5'-ATAC-GAGCTTGTTCAATACGAAGGGATGCCGTTTGGGC-CCAAGTTCGG CATAGTGTGGTGATAGTAAGAG-CAATC-3' (SEQ ID NO: 1), or a continuous sequence having 90, 91, 92, 93, 94, 95, 96, 97, 98, or 99% identity to SEQ ID NO: 1 and wherein the aptamer has selectivity for 17β-estradiol.

24. The aptamer according to claim 23 wherein the aptamer is coupled to a nanoparticle.

25. The aptamer according to claim 23, wherein the aptamer comprises a fluorescent tag.

26. The aptamer according to claim 23, wherein the aptamer comprises the sequence of SEQ ID NO: 1.

* * * * *

```
                            SEQUENCE LISTING

<160> NUMBER OF SEQ ID NOS: 1

<210> SEQ ID NO 1
    <211> LENGTH: 75
    <212> TYPE: DNA
    <213> ORGANISM: Artificial Sequence
    <220> FEATURE:
    <223> OTHER INFORMATION: Synthetic polynucleotide

<400> SEQUENCE: 1
atacgagctt gttcaatacg aagggatgcc gtttgggccc aagttcggca tagtgtggtg      60
atagtaagag caatc                                                       75
```